United States Patent [19]

Zimmerman et al.

[11] Patent Number: 5,238,919
[45] Date of Patent: Aug. 24, 1993

[54] PEPTIDES THAT INHIBIT VON WILLEBRAND FACTOR BINDING TO THE PLATELET SPIB RECEPTOR

[75] Inventors: Theodore S. Zimmerman, La Jolla, Calif.; Yoshihiro Fujimura, Kashihara, Japan; Richard A. Houghten, Solana Beach; Zaverio M. Ruggeri, La Jolla, both of Calif.

[73] Assignee: Scipps Clinic and Research Foundation, La Jolla, Calif.

[21] Appl. No.: 519,606

[22] Filed: May 7, 1990

Related U.S. Application Data

[63] Continuation-in-part of Ser. No. 270,488, Nov. 4, 1988, abandoned, which is a continuation-in-part of Ser. No. 869,188, May 30, 1986, abandoned.

[51] Int. Cl.$^5$ .................... A61K 35/16; A61K 37/02; C07K 4/08; C07K 15/14
[52] U.S. Cl. ........................... 514/8; 514/12; 514/13; 514/14; 514/822; 530/324; 530/325; 530/326; 530/383; 530/395
[58] Field of Search ................ 530/33, 330, 329, 328, 530/327, 326, 325, 324, 350; 514/8, 12, 13, 14, 15, 16, 17, 18, 19

[56] References Cited

U.S. PATENT DOCUMENTS 4,683,291  7/1987  Zimmerman et al. .............. 530/326

OTHER PUBLICATIONS

Lehninger, Biochemistry 2nd Ed., Worth Publishers, Inc., pp. 98-108 (1981).
Watson et al., Mol. Biol. of the Gene, 4th ed., Benjamin/Cummings Publishing Co. p. 46 (1987).
Pierschbacher et al., Nature, vol. 309, pp. 30-33 (1984).
Fujimura et al., The Journal of Biological Chemistry vol. 261, No. 1, pp. 381-385, 1986.
Rudinger, Peptide Hormones, pp. 1-7, Parsons (ed.), U Park Press, Baltimore (1976).
Creighton, Proteins, W. H. Freeman and Co., New York, pp. 25-27, 29-30, 33, 35, 37-42, 50, 100 (1983).
Lewin, Genes, 2nd ed., John Wiley & Sons, pp. 189, 282-293, 1985.
Concise Encyclopedia of Biochemistry, Walter de Gruyten, Berlin, New York p. 331 (1983).
Fujimura et al., J. Biol. Chem., vol. 262, No. 4, pp. 1734-1739, 1987.
Mohri et al., J. of Biol. Chem., vol. 263, No. 34, pp. 17901-17904, 1988.
Mohri et al., J. of Biol. Chem., vol. 264, No. 29, pp. 17361-17367, 1989.

*Primary Examiner*—Lester L. Lee
*Assistant Examiner*—Avis Davenport
*Attorney, Agent, or Firm*—Martin F. Savitzky; Alexis Barron

[57] ABSTRACT

This invention provides a peptide fragment of human von Willebrand Factor (vWF) and sub-fragment thereof isolated as enzymtic digestion products from naturally occurring human vWF, or isolated from synthetic peptide mixtures or isolated from lysates of organisms capable of producing recombinant human vWF. The fragments and sub-fragments are useful in the prevention and treatment of cardiovascular disorders by virtue of their ability to inhibit the binding of vWF to platelets, heparin and/or collagen.

28 Claims, 11 Drawing Sheets

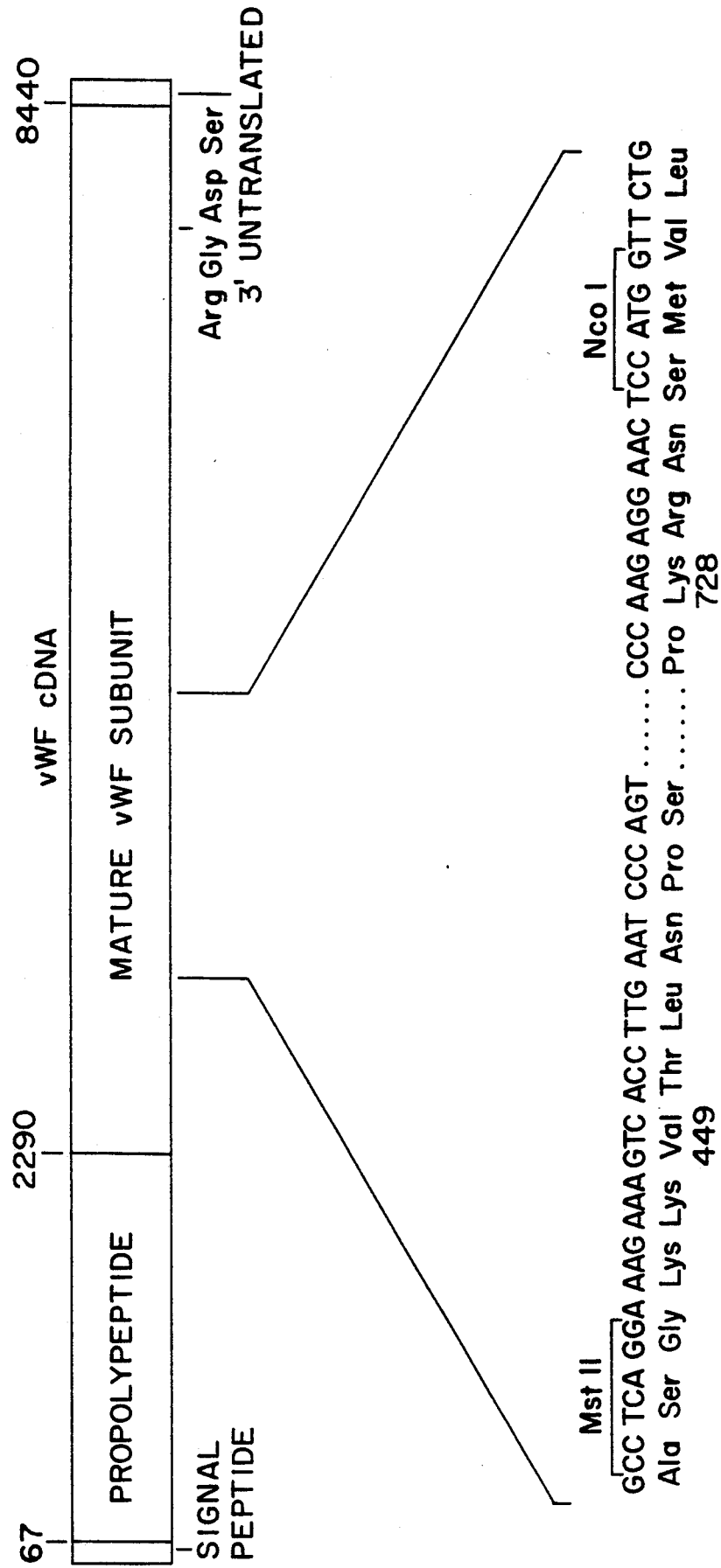

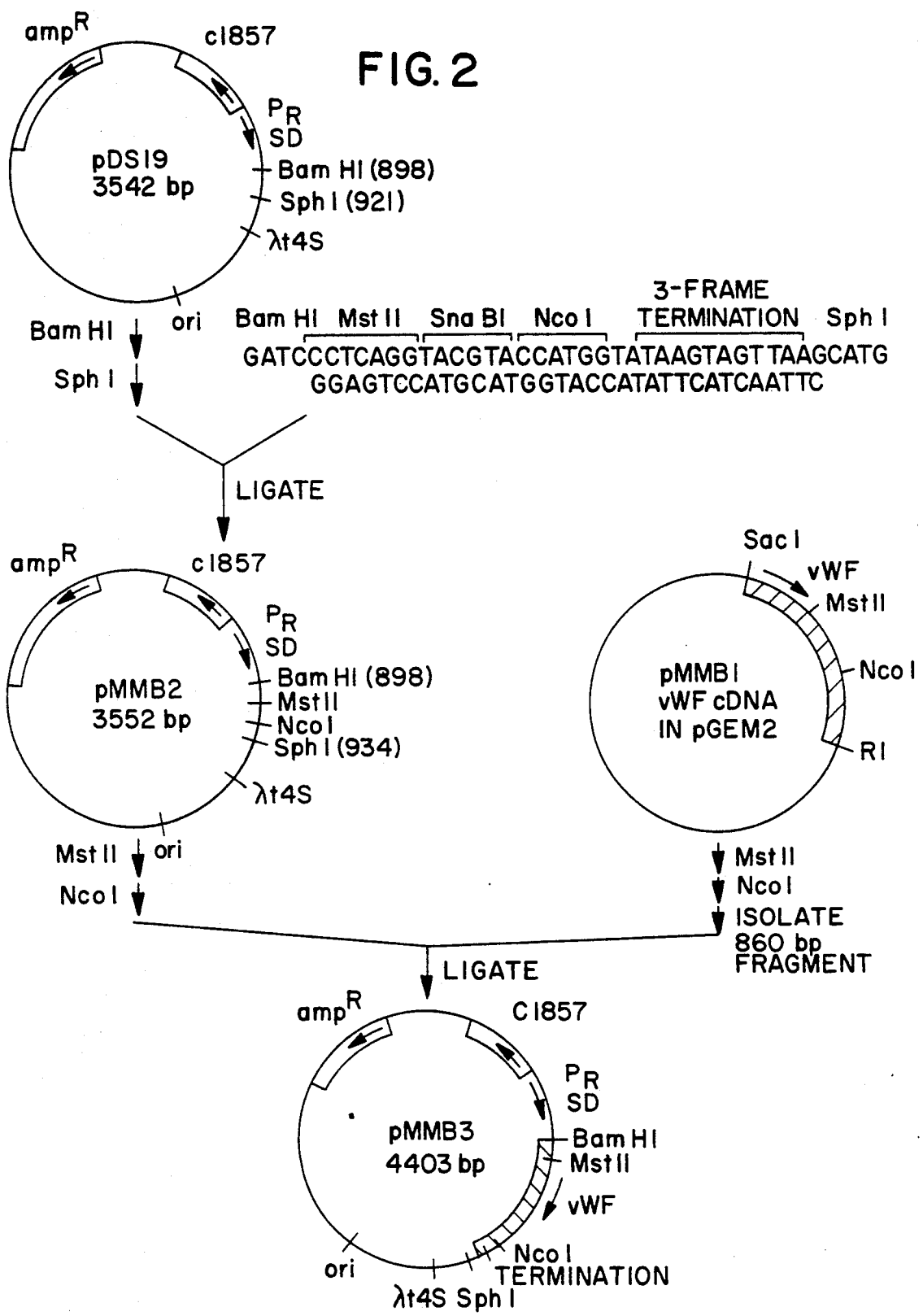

```
                            27                                                54
ATG GAT CCC TCA GGA AAG AAA GTC ACC TTG AAT CCC AGT GAC CCT GAG CAC TGC
 M   D   P   S   G   K   K   V   T   L   N   P   S   D   P   E   H   C 81                                               108
CAG ATT TGC CAC TGT GAT GTT GTC AAC CTC ACC TGT GAA GCC TGC CAG GAG CCG
 Q   I   C   H   C   D   V   V   N   L   T   C   E   A   C   Q   E   P 135                                               162
GGA GGC CTG GTG GTG CCT CCC ACA GAT GCC CCG GTG AGC CCC ACC ACT CTG TAT
 G   G   L   V   V   P   P   T   D   A   P   V   S   P   T   T   L   Y 189                                               216
GTG GAG GAC ATC TCG GAA CCG CCG TTG CAC GAT TTC TAC TGC AGC AGG CTA CTG
 V   E   D   I   S   E   P   P   L   H   D   F   Y   C   S   R   L   L 243                                               270
GAC CTG GTC TTC CTG CTG GAT GGC TCC TCC AGG CTG TCC GAG GCT GAG TTT GAA
 D   L   V   F   L   L   D   G   S   S   R   L   S   E   A   E   F   E 297                                               324
GTG CTG AAG GCC TTT GTG GTG GAC ATG ATG GAG CGG CTG CGC ATC TCC CAG AAG
 V   L   K   A   F   V   V   D   M   M   E   R   L   R   I   S   Q   K 351                                               378
TGG GTC CGC GTG GCC GTG GTG GAG TAC CAC GAC GGC TCC CAC GCC TAC ATC GGG
 W   V   R   V   A   V   V   E   Y   H   D   G   S   H   A   Y   I   G 405                                               432
CTC AAG GAC CGG AAG CGA CCG TCA GAG CTG CGG CGC ATT GCC AGC CAG GTG AAG
 L   K   D   R   K   R   P   S   E   L   R   R   I   A   S   Q   V   K 459                                               486
TAT GCG GGC AGC CAG GTG GCC TCC ACC AGC GAG GTC TTG AAA TAC ACA CTG TTC
 Y   A   G   S   Q   V   A   S   T   S   E   V   L   K   Y   T   L   F 513                                               540
CAA ATC TTC AGC AAG ATC GAC CGC CCT GAA GCC TCC CGC ATC ACC CTG CTC CTG
 Q   I   F   S   K   I   D   R   P   E   A   S   R   I   T   L   L   L 567                                               594
ATG GCC AGC CAG GAG CCC CAA CGG ATG TCC CGG AAC TTT GTC CGC TAC GTC CAG
 M   A   S   Q   E   Q   Q   R   M   S   R   N   F   V   R   Y   V   Q 621                                               648
GGC CTG AAG AAG AAG AAG GTC ATT GTG ATC CCG GTG GGC ATT GGG CCC CAT GCC
 G   L   K   K   K   K   V   I   V   I   P   V   G   I   G   P   H   A 675                                               702
AAC CTC AAG CAG ATC CGC CTC ATC GAG AAG CAG GCC CCT GAG AAC AAG GCC TTC
 N   L   K   Q   I   R   L   I   E   K   Q   A   P   E   N   K   A   F 729                                               756
GTG CTG AGC AGT GTG GAT GAG CTG GAG CAG CAA AGG GAC GAG ATC GTT AGC TAC
 V   L   S   S   V   D   E   L   E   Q   Q   R   D   E   I   V   S   Y 783                                               810
CTC TGT GAC CTT GCC CCT GAA GCC CCT CCT CCT ACT CTG CCC CCC GAC ATG GCA
 L   C   D   L   A   P   E   A   P   P   P   T   L   P   P   D   M   A 837                                               864
CAA GTC ACT GTG GGC CCG GGG CTC TTG GGG GTT TCG ACC CTG GGG CCC AAG AGG
 Q   V   T   V   G   P   G   L   L   G   V   S   T   L   G   P   K   R

891
AAC TCC ATG GTA TAA GTA GTT AAG CAT GC
 N   S   M   V   .   V   V   K   H
```

FIG. 3

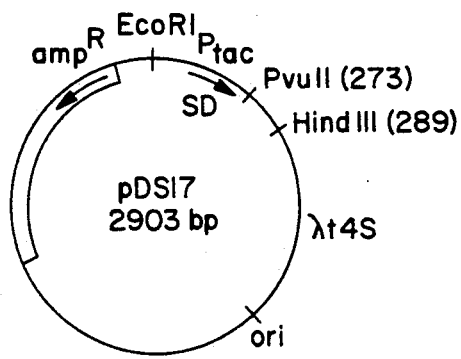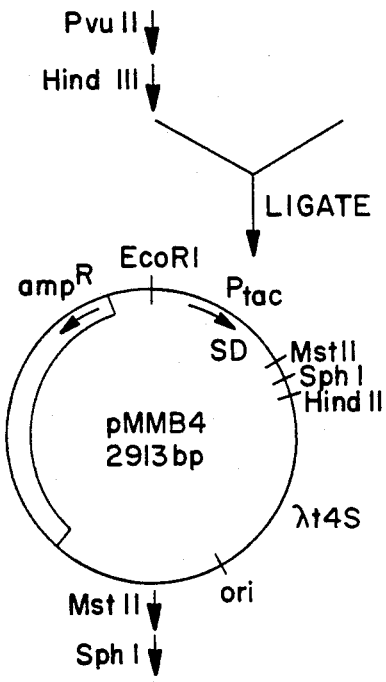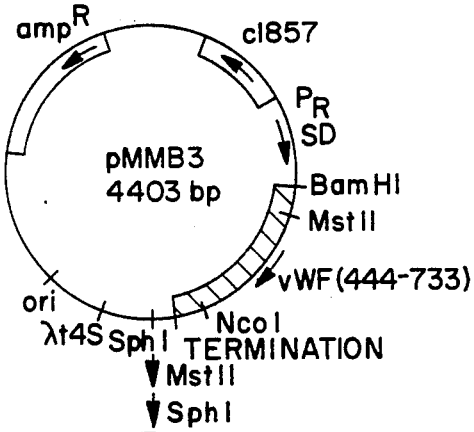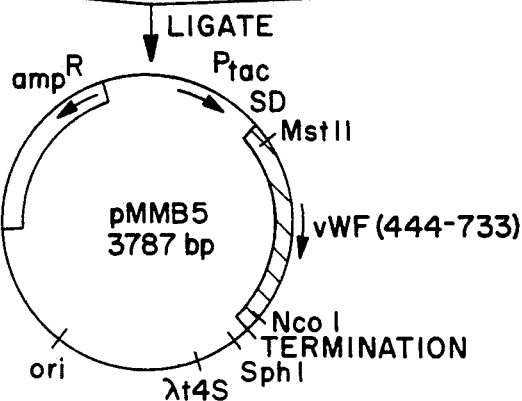
FIG. 4

FIG. 5
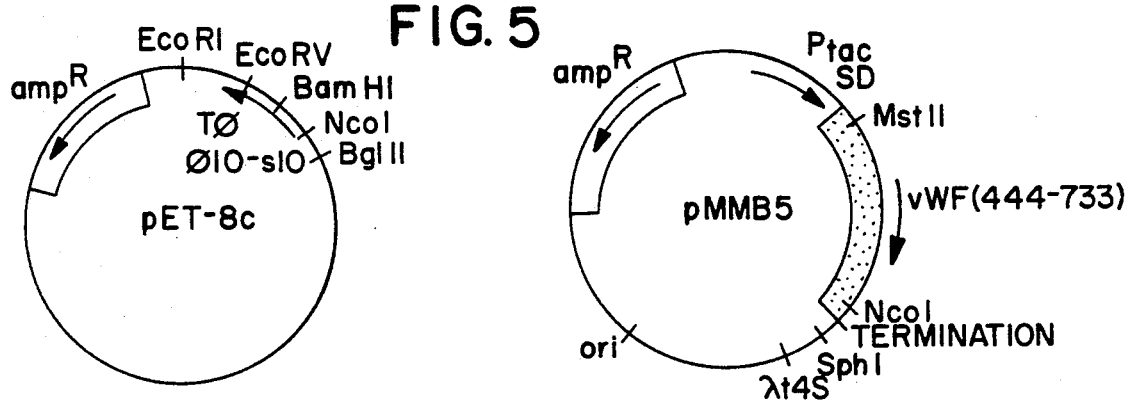
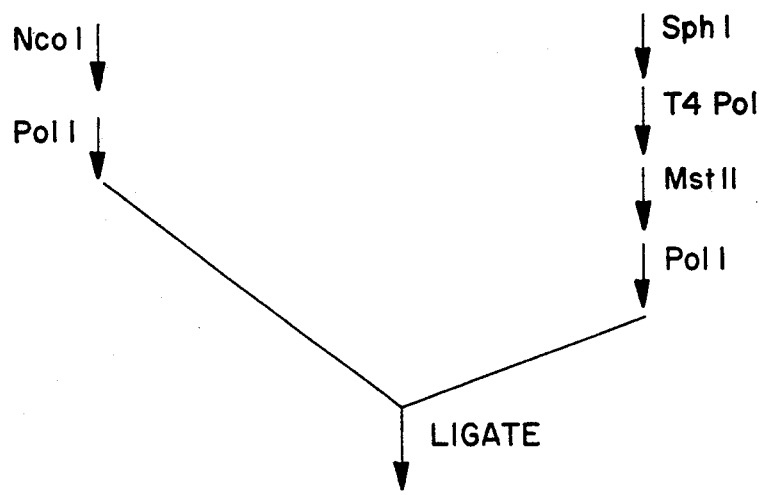
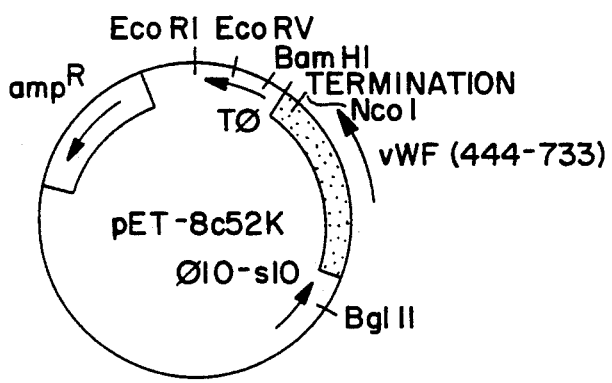

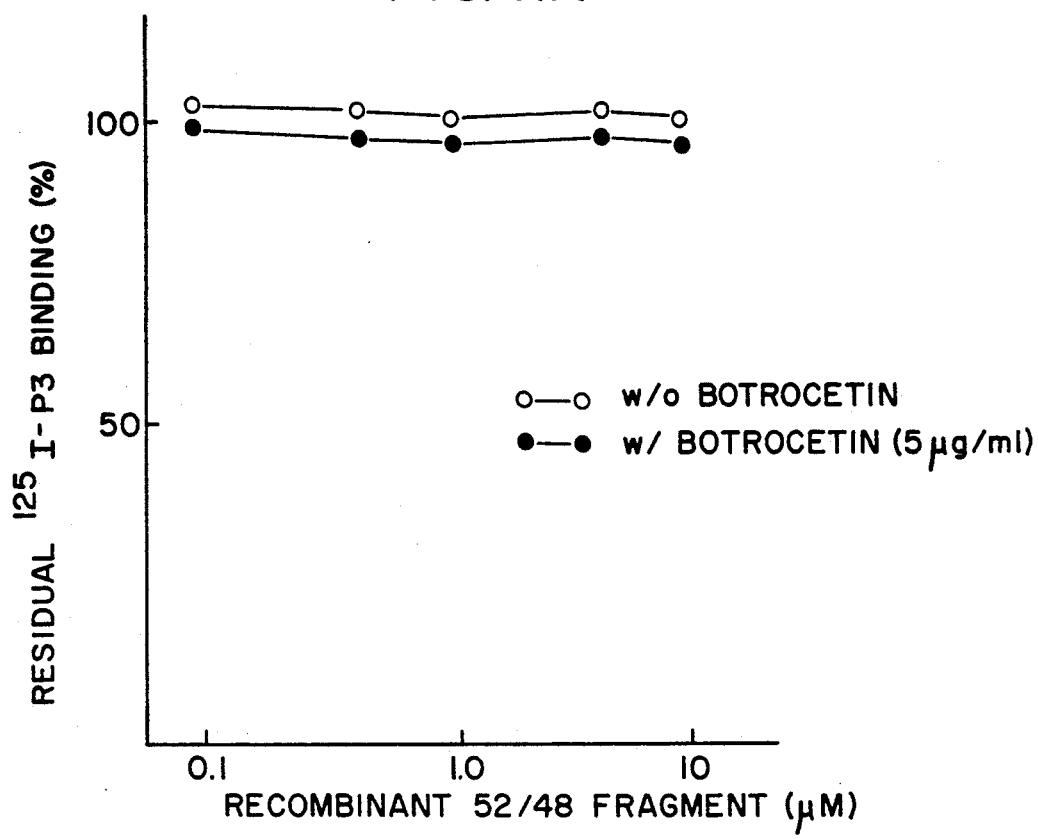
FIG. IIA
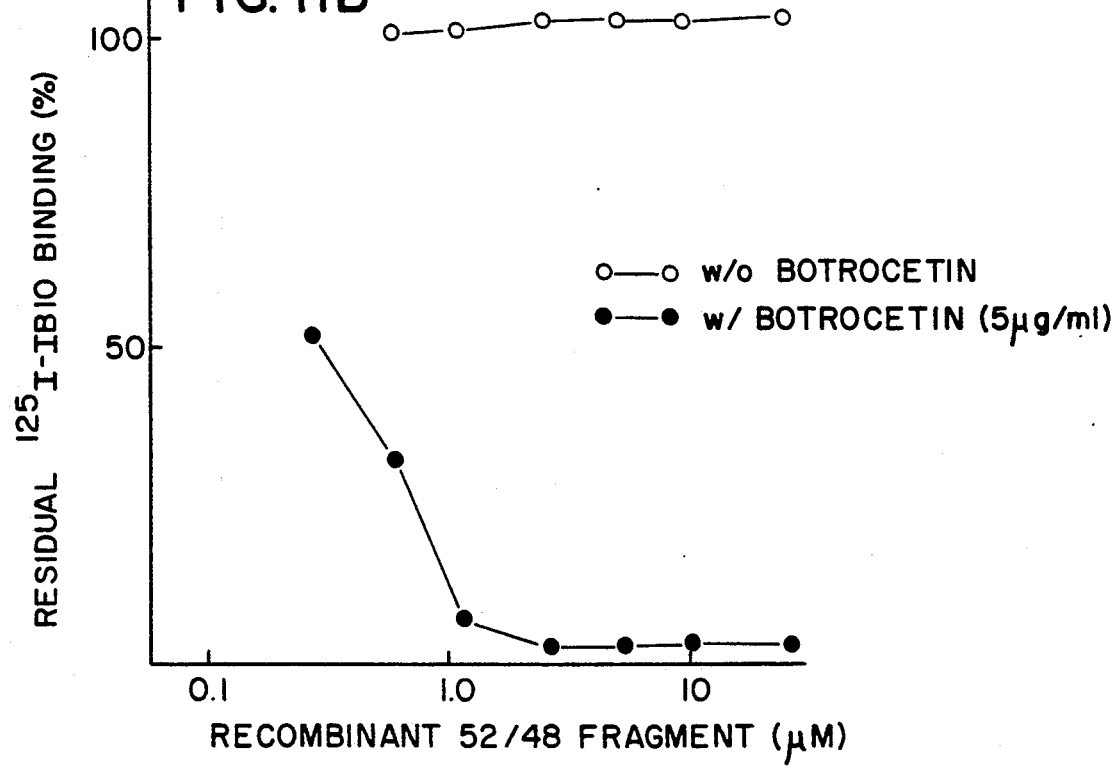
FIG. IIB

PEPTIDES THAT INHIBIT VON WILLEBRAND FACTOR BINDING TO THE PLATELET SPIB RECEPTOR

This invention was made with government support under HL 15491 and HL 31950, awarded by the National Institutes of Health. The government has certain rights in the invention.

CROSS REFERENCE TO RELATED APPLICATIONS

This application is a continuation-in-part of copending application Ser. No. 270,488, filed Nov. 4, 1988 (now abandoned), which is a continuation of application Ser. No. 869,188, filed May 30, 1986, now abandoned.

FIELD OF THE INVENTION

This invention relates generally to peptides corresponding to natural products, the cloning of structural genes and the use of such genes in the recombinant DNA-directed synthesis of protein products which are useful in the prevention and treatment of cardiovascular disorders such as thrombosis.

The deposition of platelets at the site of vessel injury or malformation is thought to play an important role in thrombus formation in a number of thrombosis disease states including coronary artery occlusion and stroke. In addition, it may contribute to the occlusion of arterial grafts which can occur when either autologous vein segments or woven artificial graft protheses are used. Platelet thrombus formation may also contribute to the thrombosis which can complicate attempts to relieve vessel obstruction by angioplasty.

Therefore, there is a need for a product which prevents platelet deposition at site of vessel injury, whether the injury occurs naturally or is induced as a result of iatropic manipulation such as those mentioned above. The peptides of the present invention have the ability to interfere with these undesired platelet depositions.

This invention relates specifically to peptides which inhibit the binding of von Willebrand Factor (vWF) to platelets, heparin and collagen.

von Willebrand Factor (vWF) is a glycoprotein which is synthesized by endothelial cells and megakaryocytes and exists in plasma in multimeric forms. As a result of the initial isolation of vWF from the Factor VIIIC complex, vWF has also been variously referred to as the Factor VIII-related protein or more simply Factor VIII-R.

vWF is known to play a central mediator role in the earliest stages of platelet deposition at the site of blood vessel wall injury. When the endothelial cell lining of a blood vessel is broken, vWF is required for the subsequent adhesion of platelets to the subendothelium. vWF functions by binding to one or more components of the subendothelium which may include collagen or the heparin-like glycosaminoglycans. vWF also binds to the platelet glycoprotein (GP) Ib receptor which causes platelets to adhere to the subendothelium. Binding of vWF to the GPIb receptor in turn triggers binding of fibrinogen to the platelet GPIIb/IIIa receptor and subsequent platelet aggregation.

The biosynthesis of vWF is a complex, multistep process involving extensive transcriptional and post-translational biochemical modifications, leading to the formation of high molecular weight glycosylated multimers of up to 20 MDa in size. As a consequence of this biosynthetic complexity, the opportunities for genetic defects to occur have presented themselves, manifesting in a number of disease states characterized by alterations in structure, function or vWF concentration. The term von Willebrand disease (vWD) defines this heterogeneous group of conditions of which several different subtypes are recognized.

Substantial work on the structure, function and molecular genetics of vWF has been reported.

Reported Developments

Fujimura et al. in "von Willebrand Factor; A Reduced and Alkylated 52/48 kDa Fragment Beginning at Amino Acid Residue 449 Contains the Domain Interacting with Platelet Glycoprotein Ib", *J. Biol. Chem.* 261:381-385 (1986), partially characterized a vWF fragment but do not describe the carboxy-terminal sequence which is necessary to fully specify the fragment. Also in this paper, the property of direct binding of the fragment to the platelets was not demonstrated.

Fujimura et al. in "A 52/48 kDa Tryptic Fragment of von Willebrand Factor Which Begins With Amino Acid Residue 449 Binds to Platelet GPIb in the Absence of Ristocetin" (Abst.), Blood 66:334a (1985), do not fully specify the fragment nor the amino acid sequence responsible for the binding of the fragment to platelets.

Bockenstedt et al. in "Structural Basis of von Willebrand Factor Binding to Platelet Glycoprotein Ib and Collagen", *J. Clin. Invest.* 77:743-749 (1986) report that digestion of native vWF polymers with Staphylococcal V8 protease to yield a 285,000 Da fragment of unspecified structure and sequence that inter alia competes with $^{125}$I-vWF for binding to GPIb. This paper shows loss of activity once the fragment is alkylated and reduced.

Girma et al. in "Mapping of Distinct von Willebrand Factor Domains Interacting with GPIb and GPIIb/IIIa and with Collagen Using Monoclonal Antibodies", Blood 67(5): 1356-1366 (1986) report that a S. aureus V-8 protease digestion fragment, SpIII, representing the $NH_2$-terminal portion of vWF contains the binding domain for the platelet receptor GPIb. SpIII is heterogenous on SDS-PAGE migrating as a 320 kDa homodimer of two 170 kDa chains and as a 280 kDa species composed of a 170 kDa chain and a 104 kDa polypeptide.

Houdijk et al. in "Identification of Functional Domain on von Willebrand Factor by Binding of Tryptic Fragments to Collagen and to Platelets in the Presence of Ristocetin", Blood 67(5):1498-1503 (1986) report the identification of a 116 kDa tryptic fragment of vWF which binds to the platelet GPIb receptor.

Sakariassen et al. in "Mediation of Platelet Adhesion to Fibrillar Collagen in Flowing Blood by a Proteolytic Fragment of Human von Willebrand Factor", Blood 67(5): 1515-1518 (1986) further characterized the SpIII V-8 protease fragment described above as containing a binding site for collagen in addition to the GPIb receptor binding domain.

Chopek et al. in "Human von Willebrand Factor: A Multivalent Protein Composed of Identical Subunits", *Biochemistry* 25:3146-3155 (1986) studied the multimeric nature of the circulating form of vWF, and that the monovalent protein displayed platelet binding properties similar to the smallest multimers.

Girma et al. in "Limited Proteolysis of Human von Willebrand Factor by *Staphylococcus aureus* V-8 Protease: Isolation and Partial Characterization of a Platelet-Binding Domain", *Biochemistry* 25:3156-3163 (1986), propose a model for vWF multimer structure in which the 270 kDa subunits are linked by disulfide bonds that alternate between the two carboxy terminal and two amino-terminal regions in a head-to-head and tail-to-tail manner. Platelet binding and ristocetin co-factor activities are localized to the NH$_2$-terminal half of the 270 kDa subunit.

Handa et al. in "The von Willebrand Factor-binding Domain of Platelet Membrane Glycoprotein Ib", *J. Biol. Chem.* 261(27):12579–12585 (1986), identifying the binding domain for vWF as being localized near the NH$_2$-terminus of the α-chain of GPIb.

Hondijk et al. in "Comparison of Tryptic Fragments of von Willebrand Factor Involved in Binding to Thrombin-activated Platelets with Fragments Involved in Ristocetin-induced Binding and Binding to Collagen", *Thrombosis and Haemostasis* 56(3):391–96 (1986), conclude that the ristocetin-binding domain (RBD), the collagen-binding domain (CBD), and the thrombin-binding domain (TBD) occur in separate regions of the vWF molecule and that the order from NH$_2$-terminal to COOH-terminal is RBD to CBD to TBD.

Williams et al. in "Inhibition of von Willebrand Factor Binding to Platelets By Two Recognition Site Peptides", *Thrombosis Res.* 46:457–471 (1987), identify two recognition sites for vWF binding on platelet GPIIb/IIIa receptors; one is a tetrapeptide arg-gly-asp-ser (RGDS) and the second is a dodecapeptide of sequence HHLGGAKQAGDV.

Fujimura et al. in "A Heparin-binding Domain of Human von Willebrand Factor", *J. Biol. Chem.* 262(4):1734–39 (1987), report that the platelet GPIb-binding domain of vWf resides in a 52/48 kDa tryptic fragment beginning with amino acid residue Val-449 and ending with amino acid residue Lys-728. Further a high affinity heparin binding site was also identified within the region. The two domains are thought to be in close proximity to one another but not to be precisely congruent.

Ruggeri et al. in "von Willebrand Factor and von Willebrand Disease", *Blood* 70(4):895–904 (1987), review the structural/functional relationships of various vWF binding domains and their relationship to disease treatment protocols.

Berliner et al. in "Generation and Characterization of Peptide-specific Antibodies That Inhibit von Willebrand Factor Binding to Glycoprotein IIb/IIIa Without Interacting With Other Adhesive Molecules, *J. Biol. Chem.* 263(16):7500–7505 (1988), disclose the use of a synthetic peptide covering the sequence Glu[1737] to Ser[1750] as an antigen for the generation of antibodies capable of reacting with vWF and preventing vWF binding to platelets.

Vicente et al. in "Isolation and Functional Characterization of the vWF-binding Domain Located Between Residues His[1] and Arg[293] of the α-chain of Glycoprotein Ib", *J. Biol. Chem.* 263(34):18473–18479 (1988), define a 45 kDa tryptic fragment of glycocalicin as being a region important for the binding of vWF to platelets.

Lynch et al. in "Molecular Cloning of cDNA for Human von Willebrand Factor: Authentication by a New Method", *Cell* 41:49–56 (1985) report the identification of a 2.4 Kb partial cDNA clone of human vWF. The clone encodes a polypeptide corresponding to the COOH terminal portion of vWF and reacts immunologically with anti-human vWF antibodies.

Ginsberg et al. in "Human von Willebrand Factor (vWF): Isolation of Complementary DNA (cDNA) Clones and Chromosomal Localization", *Science* 228:1401–1406 (1985) report the identification of a series of overlapping clones which span approximately 8.2 Kb of vWF mRNA. Using the clones as probes, the vWF gene was localized to human chromosome 12 by in situ hybridization.

Sadler et al. in "Cloning and Characterization of Two cDNAs Coding for Human von Willebrand Factor", *Proc. Natl. Acad. Sci. USA* 82:6394–6398 (1985); describe a partial amino acid sequence of vWF based on two non-overlapping clones.

Shelton-Inloes et al. in "cDNA Sequences for Human von Willebrand Factor Reveal Five Types of Repeated Domains and Five Possible Protein Sequence Polymorphisms", *Biochemistry* 25:3164–3171 (1986) report the isolation of four cDNAs that span 6.5 Kb of vWF mRNA and completely specify the 2050 amino acids of the subunit of mature secreted vWF and 24 amino acids of a precursor peptide. Domain A consisting of 193–220 amino acids present in three tandem repeats between residues 497–1111 lies within a 50 kDa tryptic fragment of vWF that binds to GPIb of resting platelets.

Titani et al. in "Amino Acid Sequence of Human von Willebrand Factor", *Biochemistry* 25:3171–3148 (1986), report the complete amino acid sequence of human vWF and identify the platelet glycoprotein Ib binding domain as being localized between residues 449–728 of the vWF monomer.

Bonthron et al. in "Structure of Pre-pro-von Willebrand Factor and its Expression in Heterologous Cells", *Nature* 324:270–273 (1986), disclose the successful heterologous expression of a 2,813 amino acid pre-pro vWF protein.

Fretto, et al. in "Substructure of Human von Willebrand Factor", *J. Biol. Chem.* 261(33):15679–689 (1986), confirm the localization of the platelet binding domain in the NH$_2$-terminal half of the vWF molecule.

Pareti, et al. in "Isolation and Characterization of Collagen Binding Domain in Human von Willebrand Factor", *J. Biol. Chem.* 261(32):15310–15315 (1986) and "Isolation and Characteristics of Two Domains of Human von Willebrand Factor That Interact with Fibrillar Collagen Types I and III", *J. Chem.* 262(28):13835–13841 (1987), described a number of tryptic and V8 protease fragments capable of binding collagen inter alia the 52/48 vWF fragment disclosed herein.

Collins et al. in "Molecular Cloning of the Human Gene for von Willebrand Factor and Identification of the Transcription Inhibition Site", *Proc. Nat'l. Acad. Sci. USA* 84:4393–97 (1987), report the isolation of a series of overlapping cosmid genomic clones containing the entire coding region of the human gene for von Willebrand Factor.

Titani et al. in "Amino Acid Sequence of the von Willebrand Factor-binding Domain of Platelet Membrane Glycoprotein Ib, *Proc. Nat'l. Acad. Sci. USA* 84:5610–5614 (1987) disclose the complete amino sequence in a 293 amino acid region of the α-chain of GPIb that mediates vWF binding.

Mohri et al. in "Structure of the vWF Domain Interacting with Glycoprotein Ib", *J. Biol. Chem.* 263(34):17901–17904 (1988), provide evidence that binding of GPIb to vWF involves two limited non-contiguous regions of vWF each approximately 15 amino acids long and separated by a linear sequence of some 200 amino acids.

Sixma et al. in "Functional Effects of Deletion of the A-1 Domain of vWF by Site Directed Mutagenesis", (Abst) *Arteriosclerosis* 8(5):697(a) (1988), report the construction of a deletion mutant of vWF cDNA in which the A-1 domain (i.e. the region from residue 476 to 717) had been removed. The product recovered from the supernatant of transiently infected COS-1 cells with such a mutant was incapable of binding to heparin or to platelets in the presence of ristocetin.

Mohri et al. in "Isolation of the vWF Domain Interacting with Platelet Glycoprotein Ib, Heparin and Collagen and Characterization of Its Three Distinct Functional Sites", *J. Biol. Chem.* 264(29):17361-67 (1989), report further details of the structural relationship of three vWF binding domains, including that a dimer of the GPIb site is required for ristocetin-induced platelet aggregation.

Sequences reported to be important in heparin binding of anti-thrombin III, histidine rich glycoprotein and apoliprotein E, proteins unrelated in structure and function to vWF were published by Cardin et al. in "Binding of a High Reactive Heparin to Human Apoliprotein E: Identification of Two Heparin-binding Domains", *Biochem. Biophys. Res. Comm.* 134:783-789 (1986); by Koide et al. in "The Heparin-binding Site(s) of Histidine-rich Glycoprotein as Suggested by Sequence Homology With Antithrombin III", *Febs. Lett.* 194:242-244 (1986); by Koide et al. in "The N-terminal Sequence of Human Plasma Histidine-rich Glycoprotein Homologous to Antithrombin With High Affinity for Heparin", *Febs. Lett.* 141:222-224 (1982), and by Koide et al. in "Antithrombin III Toyama: Replacement of Arginine-47 by Cysteine in Hereditary Abnormal Antithrombin III That lacks Heparin-binding Ability", *Proc. Natl. Acad. Sci. USA* 81:289-293 (1984).

Summary of the Invention

In one aspect this invention provides a polypeptide capable of inhibiting the binding of von Willebrand Factor to platelets, heparin and collagen consisting essentially of an amino acid sequence corresponding to a von Willebrand Factor fragment having an amino-terminal residue about amino acid 449 Val and having a carboxy-terminal residue about amino acid 728 Arg.

In a further aspect this invention provides a peptide capable of inhibiting the binding of von Willebrand Factor to platelets having an amino acid sequence consisting essentially of:

In a further aspect this invention provides a therapeutic composition comprising effective amounts of polypeptides which inhibit binding of vWF to platelets, heparin and collagen in a patient, in association with a pharmaceutically acceptable carrier.

In a further aspect this invention provides methods for inhibiting thrombosis.

In a further aspect this invention provides a DNA sequence encoding a fragment of human vWF, said fragment consisting essentially of an amino acid sequence having an amino-terminal residue at about 449 Val and having a carboxy-terminal residue at about 728 Arg.

In a further aspect this invention provides an expression vector comprising a human DNA encoding a portion of vWF consisting essentially of an amino-terminal residue at about 449 Val and a carboxy-terminal residue at about 728 Arg.

In a further aspect this invention provides a recombinant host transformed with an expression vector comprising a human DNA encoding a portion of vWF consisting essentially of an amino-terminal residue at about 449 Val and a carboxy-terminal residue at about 728 Arg.

In a final aspect this invention provides a process for the production of a fragment of human vWF comprising culturing a host organism transformed with an expression vector comprising a human DNA encoding a portion of vWF consisting essentially of an amino-terminal residue at about 449 Val and a carboxy-terminal residue at about 728 Arg under conditions of time, temperature and pH sufficient to permit the expression of human vWF fragment by said culture and recovering the fragment therefrom.

BRIEF DESCRIPTION OF THE DRAWINGS

FIG. 1 is a diagramatic illustration of the vWF gene. The location of the cDNA of the invention is indicated within the coding region of the mature vWF subunit.

FIG. 2 is a diagramatic illustration of the cloning strategy used to construct plasmid pMMB3, a plasmid useful in practicing the invention.

FIG. 3 is the complete coding sequence for vWF fragment in pMMB3.

| | | |
|---|---|---|
| LCDLAPEAPPPTLPP; | PEAPPPTLPPDMAQV; | VKYAGSQVASTSEVL; |
| SDPEHCQICHCDVVN; | DCVVNLTCEACQEPG; | CQEPGGLVVPPTDAP; |
| PTDAPVSPTTLYVED; | RIASQVKYAGSQVAS; | PSERLRRIASQVKYAG; |
| DMMERLRISQKWVRV; | EFEVLKAFVVDMMER; | KAFVVDMMERLRISQ; |
| HDGSHAYIGLKDRKR; | QIFSKIDRPEASRIA; | LYVEDISEPPLHDFY; |
| VSPTTLYVEDISEPP; | AYIGLKDRKRPSELR; | KDRKRPSELRRIASQ; |
| ASRIALLLMASQEPQ; | RMSRNFVRYVQGLKK; | VTLNPSDPEHCQICH; |
| CQICHCDVVNLTCEA; | IPVGIGPHANLKQIR; | GPHANLKQIRLIEKQ; |
| SVDELEQQRDEIVSY; | EIVSYLCDLAPEAPP; | PTLPPDMAQVTVGPG; |
| TVGPGLLGVSTLGPK; | LIEKQAPENKAFVLS or | APENKAFVLSSVDEL and |
| combinations thereof. | | |

In a further aspect this invention provides a peptide capable of inhibiting the binding of von Willebrand Factor to heparin having an amino acid sequence consisting essentially of:

FIG. 4 is a diagramatic illustration of the cloning strategy used to construct plasmid pMMB5, a plasmid useful in practicing the invention.

| | | |
|---|---|---|
| KDRKRPSELRRIASQ; | LIEKQAPENKAFVLS; | SQEPQRMSRNFURYV; |
| KYTLFQIFSKIDRPE; | DMMERLRISQKWVRV; | LYVEDISEPPLHDFY; |
| ISEPPLHDFYCSRLL; | SQEPQRMSRNFVRYV; | IPVGIGPHANLKQIR; |
| GPHANLKQIRLIEKQ; | LKQIRLIEKQAPENK or | TVGPGLLGVSTLGPK and |
| combinations thereof. | | |

FIG. 5 is a diagramatic illustration of the cloning strategy used to construct plasmid pET-8c52K, a plasmid useful in practicing the invention.

Figure 6:
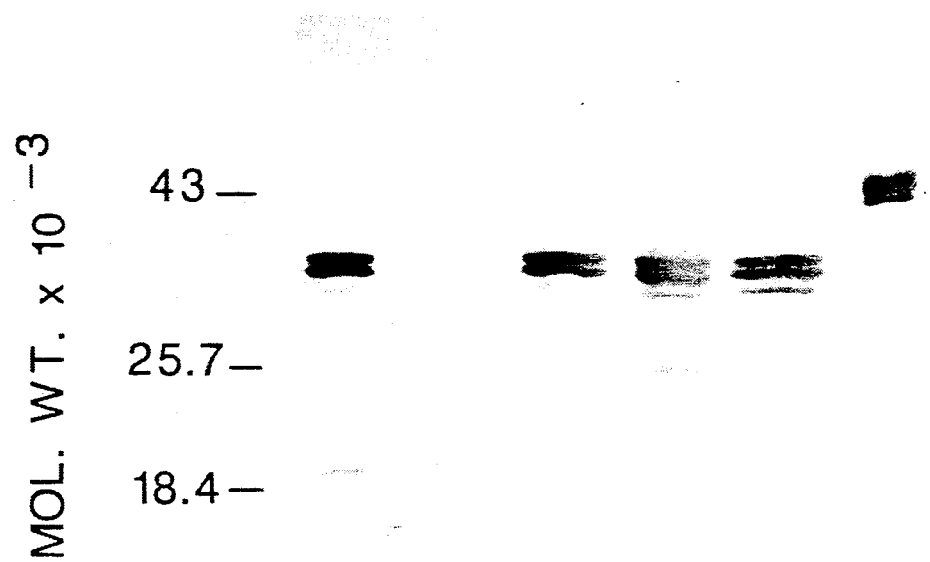

FIG. 6 is an illustration of a western blot depicting immunoreactive 33 kD vWF fragment at various steps in the initial purification from the bacterial lysate. The total amount of protein loaded per lane, in lanes 1-5 is 40 micrograms. Lane 6 contains 100 nanograms of the 52 kD tryptic fragment of native vWF. The western blot was reacted with a mouse monoclonal antibody to the 52 kD tryptic fragment of native vWF. Detection was achieved using a biotin labeled goat anti mouse IGG second antibody, and an avidin-biotin-horseradish peroxidase complex. Lane 1 is from total bacterial lysate. Lane 2 is supernatant from centrifuged bacterial lysate. Lane 3 is the pellet from centrifuged bacterial lysate. Lane 4 is the supernatant from a 2M urea wash and centrifugation of previous pellet. Lane 5 is the pellet from the 2M urea wash and centrifugation.

Figure 7:
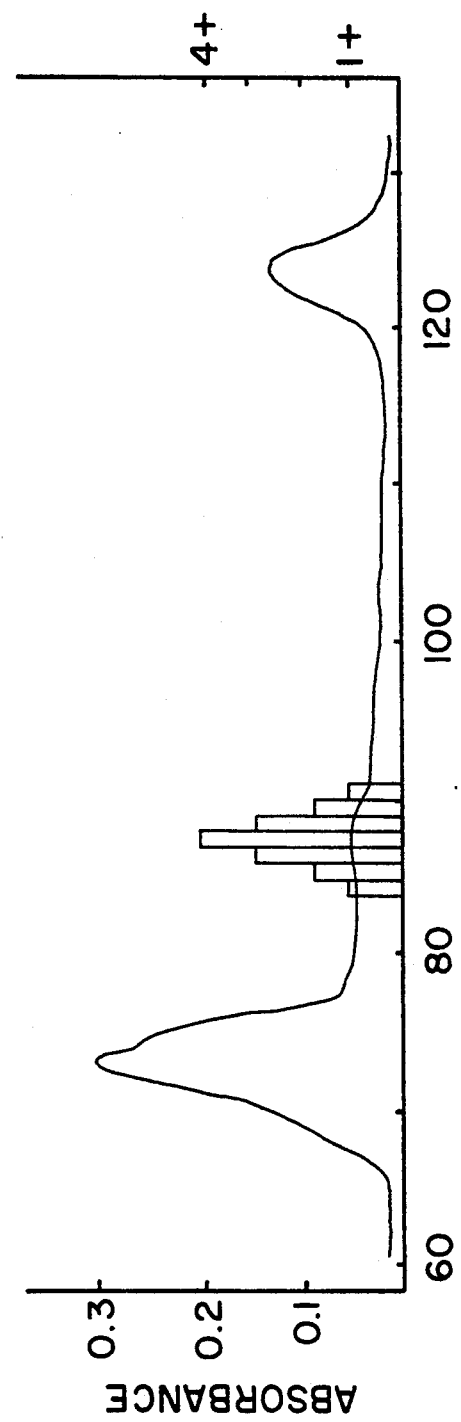

FIG. 7 is an illustration of a gel filtration elution profile of a crude *E. coli* lysate.

Figure 8:
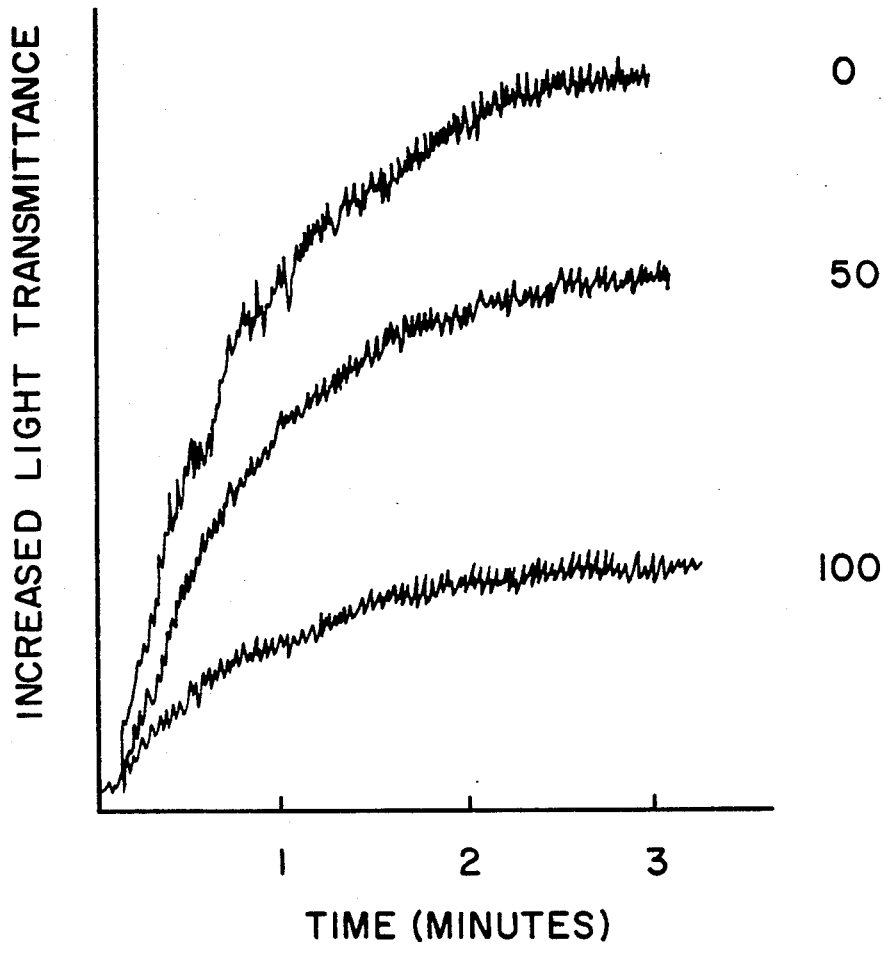

FIG. 8 is an illustration of the effect of a recombinant peptide of the invention on ristocetin-induced platelet aggregation.

Figure 9:
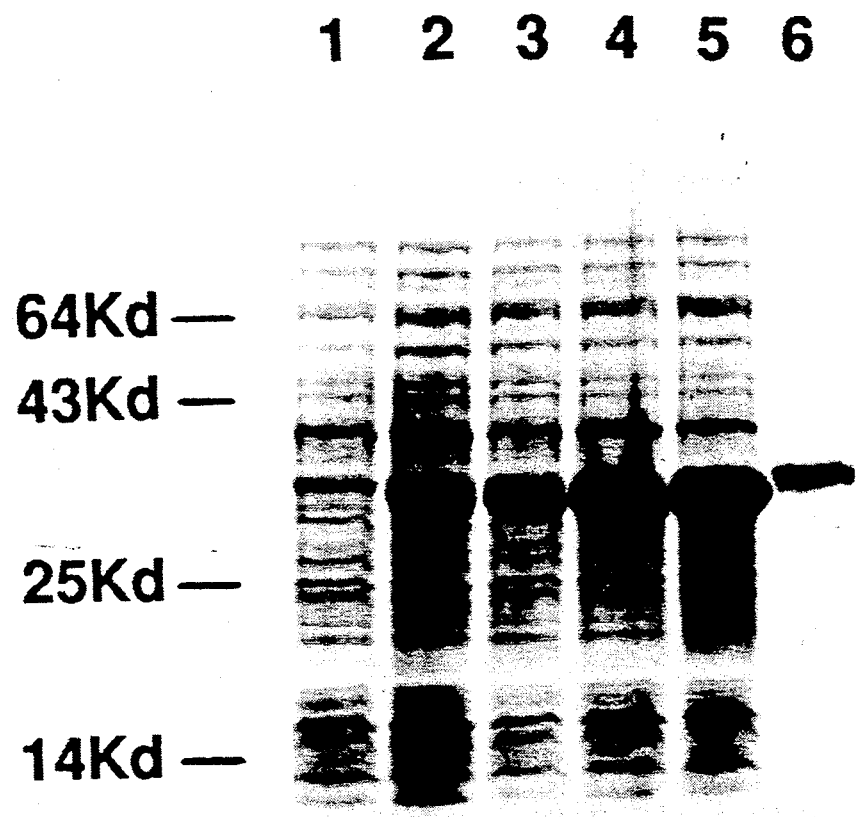

FIG. 9 is an illustration of a Western blot analysis of the T7 expression product with an illustration of essentially homogeneous vWF fragment (lane 6).

Figure 10A:
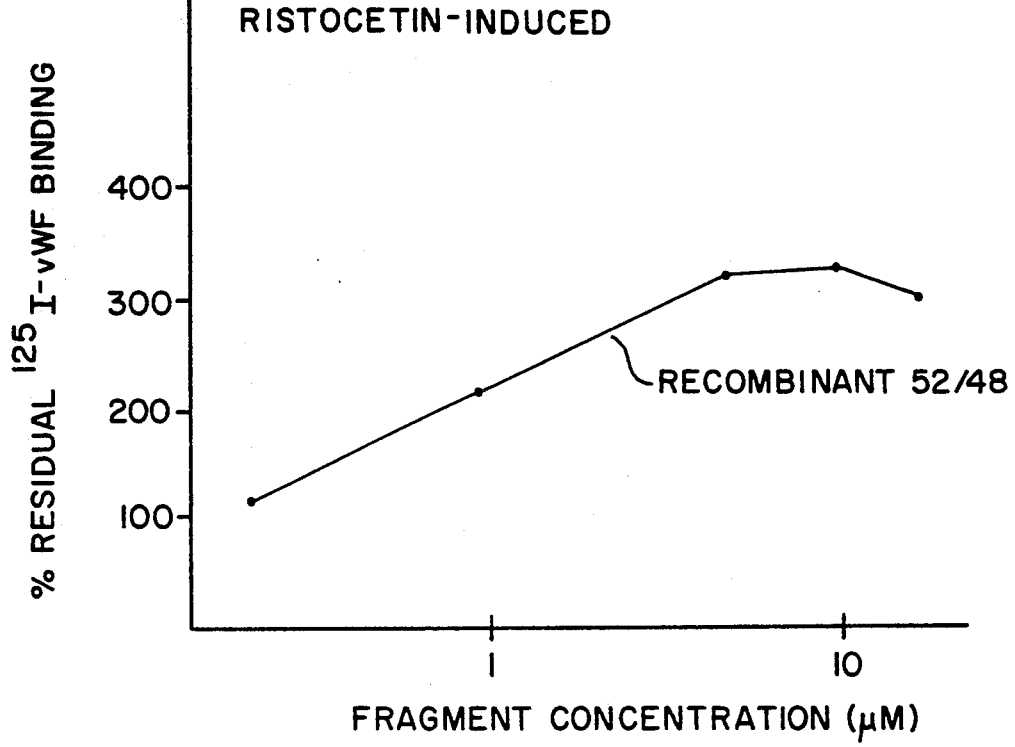
Figure 10B:
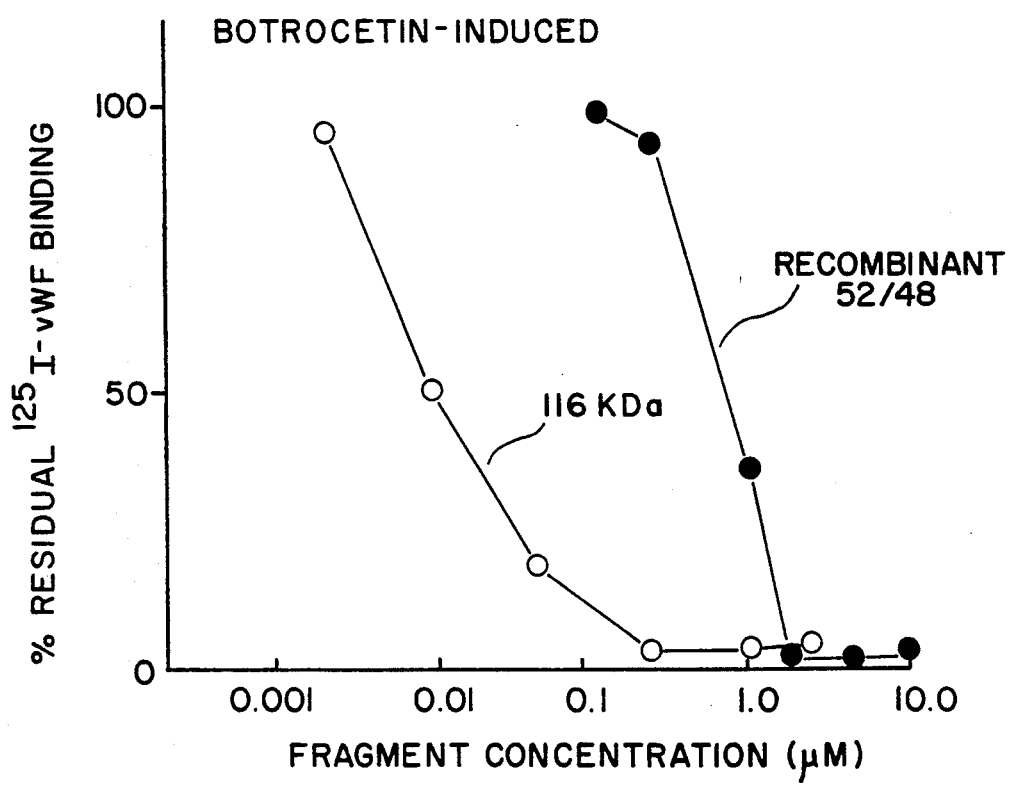

FIG. 10 illustrates the inhibiting activity of recombinantly produced vWF fragment in a ristocetin (10A) and a botrocetin (10B) assay system.

FIG. 11 illustrates the binding of the recombinantly produced vWF fragment to GPIb by means of inhibitor antibody probes.

FIG. 11*a* is a graphical representation of the binding of the noninhibitory anti-glycoprotein Ib antibody (LJ-P3) to platelets in the presence and absence of botrocetin.

FIG. 11*b* is a graphical representation of the binding of the inhibitory anti-glycoprotein IB antibody (LJ-Ib10) to platelets in the presence and absence of botrocetin.

DETAILED DESCRIPTION OF THE INVENTION

As used herein the following terms have the following meanings:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and the combination of base and sugar is called a nucleoside. The base characterizes the nucleoside. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses. Heterologous DNA is DNA which can be introduced into a host organism from a source that does not normally exchange DNA with that host. e.g. human DNA used to transform *E. coli*.

Codon—A DNA sequence of three nucleotides (a triplet) which encodes through mRNA an amino acid, a translation start signal or a translation termination signal. For example, the DNA nucleotide triplets TTA, TTG, CTT, CTC, CTA and CTG encode the amino acid leucine ("Leu"), TAG, TAA and TGA are translation stop signals and ATG is a translation start signal.

Reading Frame—The grouping of codons during translation of mRNA into amino acid sequences. During translation the proper reading frame must be maintained. For example, the DNA sequence GCTGGTTGTAAG theoretically may be expressed in three reading frames or phases, each of which affords a different amino acid sequence:

<u>GCT</u> <u>GGT</u> <u>TGT</u> <u>AAG</u>———Ala—Gly—Cys—Lys
G <u>CTG</u> <u>GTT</u> <u>GTA</u> AG—Leu—Val—Val
GC <u>TGG</u> <u>TTG</u> <u>TAA</u> G———Trp—Leu—(STOP)

However, only one of the above reading frames encodes the correct genetic information. The translational start signal is recognized by the ribosome and accessory initiation factors to fix the correct reading frame.

Polypeptide—A linear array of amino acids connected one to the other by peptide bonds between the α-amino and carboxy groups of adjacent amino acids.

Genome—The entire DNA of a cell or a virus. It includes inter alia the structural genes coding for individual polypeptides as well as regulatory sequences such as operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide. Structural genes may also have RNAs as their primary product such as transfer RNAs (tRNAs) or ribosomal RNAs (rRNAs).

Transcription—The process of producing RNA from a structural gene.

Translation—The process of producing a polypeptide from mRNA.

Expression—The process undergone by a structural gene to produce a product. In the case of a protein product it is a combination of transcription and translation.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (Tet$^R$) transforms a cell previously sensitive to tetracycline into one which is resistant to it. A cell transformed by a plasmid is called a "transformant".

Phage or Bacteriophage—Bacterial virus many of which consist of DNA sequences encapsulated in a protein envelope or coat ("capsid").

Cloning Vehicle—A plasmid, phage DNA or other DNA sequence which is able to replicate in a host cell, characterized by one or a small number of endonuclease recognition sites at which such DNA sequences may be cut in a determinable fashion for the insertion of heterologous DNA without attendant loss of an essential biological function of the DNA, e.g., replication, production of coat proteins or loss of expression control regions such as promoters or binding sites, and which contain a selectable gene marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction or DNA replication.

Replicon—DNA required for replication in a particular organism, includes an origin of replication.

Recombinant DNA Molecule—A molecule consisting of segments of DNA from different genomes which have been joined end-to-end and have the capacity to infect some host cell and be maintained therein.

Expression Control Secuence—A sequence of nucleotides that controls and regulates expressing of structural genes when operatively linked to those genes. They include the lac system, major operator and promoter regions of phage lambda, the control region of fd coat protein and other sequences known to control the expression of genes of prokaryotic or eukaryotic cells and their viruses.

Mutation—A hereditable change in the genetic information of an organism.

Mutant—An organism harboring a mutation. Generally expressing a discernible phenotype when compared to a standard reference strain of the species to which the organism belongs or to a wild-type population of that organism.

Peptide Sub-fragment—Any portion of a peptide fragment which retains biological activity. For example the vWF fragment of this invention is a peptide comprising about 280 amino acids. The bioactive peptides of 15-20 amino acids constitute sub-fragments of this larger peptide. The sub-fragment may be of any length from 15-20 amino acids up to but not including the full-length 280 amino acid fragment.

As indicated, the present invention encompasses a 52/48 kDa polypeptide fragment which inhibits binding of vWF to platelets, heparin and collagen. This particular fragment was isolated as tryptic fragment of vWF that migrates in SDS-polyacrylamide gel electrophoresis (SDS-PAGE), under reducing conditions, as a 52/48 kDa doublet. The amino-terminal sequence, VTLNPSDPEHCQ, was found to be identical for both members of the doublet. This amino-terminal sequence was published in Fujimura et al., *J. Biol. Chem.* 261:381-385 (1986) suora. The published amino-terminal sequence was further proof that the molecular weight difference between doublet constituents was because of carbohydrate composition and established the position of this peptide within the intact vWF polypeptide of approximately 2050 amino acid residues as beginning with residue designated 449.

The characterization of the 52/48 kDa fragment by both its amino and carboxy-termini makes possible the identification of the nucleotide sequence that is essential for the expression of the fragment by recombinant DNA techniques. Through the use of such techniques the fragment is produced by bacteria, yeast, or other cells into which the nucleotide sequence for producing the fragment is inserted by techniques known to those of ordinary skill in the art. The identification of only the amino-terminal sequence of the 52/48 kDa fragment in Fujimura et al., *J. Biol. Chem.* 261:381- 385 (1986) suora, makes it impossible for one of ordinary skill in the art to express the 52/48 kDa fragment since only by knowing the amino and carboxy-termini of a peptide fragment can the nucleotide sequence that encodes for this fragment be defined.

The carboxy-terminal sequence that is required along with the amino-terminal sequence for recombinant DNA expression of the 52/48 kDa fragment was determined in the following manner. A 55 kDa fragment of vWF which was produced by the same tryptic digestion that produced the 52/48 kDa fragment was found to have NSMVLDVAFVLE as an amino-terminal sequence. This amino-terminal sequence of the 55 kDa fragment was found to be carboxy-terminal to the 52/48 kDa fragment which had already had its amino-terminal sequence determined. Given this information it can be determined that the carboxy-terminus of the 52/48 kDa fragment ends just prior to the amino-terminal sequence of the 55 kDa fragment. Based on the knowledge of the amino-terminal sequence of the 55 kDa fragment and the known published partial amino acid sequence of vWF in Sadler et al., *Proc. Nat'l. Acad. Sci. USA* 82:6394-6398 (1985) suora, the amino acid sequence of the carboxy-terminal region of the 52/48 kDa fragment was determined. This carboxy-terminal region was determined to extend no further than the amino acid residue designated 729 in the intact vWF polypeptide. For an explanation of the basis for the numbering of the amino acids comprising the intact vWF polypeptide which was used for characterizing the 52/48 kDa fragment, see Fujimura et al., *J. Biol. Chem.* 261:381-385 (1986) supra.

With such information a nucleotide sequence can be inserted into the appropriate vector for expression of the 52/48 kDa fragment. For a description of recombinant DNA techniques for cloning vWF fragments, see Ginsburg et al., *Science* 228:1401-1406 (1985) supra and Sadler et al., *Proc. Nat'l. Acad. Sci. USA* 82:6394-6398 (1985) supra.

Purified vWF for trypsin cleavage was obtained from commercial Factor VIII concentrate (Armour Pharmaceutical, Kankakee, Ill.) by immunoadsorbant chromatography using an antiv-WF monoclonal antibody coupled to SEPHAROSE 4B (Pharmacia) as described in Fulcher and Zimmerman, *Proc. Nat'l. Acad. Sci. USA* 79:1648-1652 (1982). The vWF bound to the antibody was eluted with 3M NaSCN dissolved in 0.01 M imidazole, 0.15M NaCl buffer pH 6.8, containing 0.1M L-lysine HCl and 0.02% $NaN_3$. The eluted vWF was dialyzed extensively against 0.05M Tris, 0.15M NaCl, pH 7.35 (TBS) and then concentrated by ultrafiltration with an Amicon PM-30 membrane (Amicon Corp., Danvers, Mass.). After centrifugation at $10,000 \times g$ for 30 minutes at room temperature, the preparation was subjected to HPLC size exclusion chromatography using two BioRad columns ($60 \times 2.15$ cm) mounted in series, one TSK G4000 SW and the other G3000 SW. The columns were equilibrated with 0.2M Na acetate, pH 5.5, containing 5% dimethyl sulfoxide, and run at flow rate of 4 ml/min.

Trypsin digestion was performed in 0.2M Na acetate buffer, pH 7.0, containing 0.02% $NaN_3$, at 37° C. for 2 h, using 2,5000 units of trypsin (bovine pancreatic Type I, 15,000 units/mg, Sigma)/mg of vWF. The fragments generated were separated by HPLC size exclusion chromatography in three main fractions (denominated A, B and C). Isolation of the 52/48 kDa doublet mainly contained in fraction B, as well as of other fragments of 13 kDa, 22 kDa, 41 kDa, (all from fraction B) and 55 kDa (from fraction C), was performed by HPLC chromatofocusing, salt gradient elution, and size exclusion chromatography, all in the presence of 6M urea. Reduction and S-carboxy methylation of proteins was achieved by treatment with dithiothreitol, in equal amount (w/w) to protein, for 1h at 37° C., followed by treatment with a 2.7-fold excess (w/w) of iodoacetamide, for 30 minutes at room temperature (22°-25° C.) and in the dark.

All samples were finally dialyzed extensively against a buffer composed of 0.05M Tris, 0.15M NaCl, pH 7.35, concentrated by ultrafiltration (Amicon Corp., Danvers, Mass.), and dialyzed again before storage at −70° C. The tryptic fragments of vWF were analyzed by polyacrylamide gel electrophoresis in the presence of sodium dodecyl sulfate (SDS-PAGE) using 5-15% or 10-15% linear gradient gels, under reducing and non-reducing conditions, as recently described. The gels were stained with Coomassie brilliant blue-R (Bio-Rad Laboratories). The NH2-terminal sequence analysis of each of the purified fragments was performed using a gas-phase sequenator (Model 470A, Applied Biosystems, Foster City, Calif.). Identification of the phenylthiohydantoin amino acid derivatives was achieved by reverse phase chromatography, in an HPLC system (Perkin-Elmer, Norwalk, Conn.), using a ZORBAX PTH column (E.I. du Pont de Nemours) following the manufacturer's instructions.

Peptides 15 amino acid residues in length beginning from the carboxy-terminal region of the 52/48 fragment were synthesized as described by Houghton et al. in "General Method for the Rapid Solid-phase Synthesis of Large Numbers of Peptides: Specifically of Antigen-antibody Interaction at the Level of Individual Amino Acids", *Proc. Nat'l. Acad. Sci. USA* 82:5131-5135 (1985).

In the well known procedure for solid-phase synthesis of a peptide, the desired peptide is assembled starting from an insoluble support such as benzhydryl amine or chloromethylated resin (derived from cross-linked polystyrene, and available from chemical supply houses). The amino acid at the carboxyl-terminal end of the desired polypeptide, carrying protecting groups on the alpha-amino nitrogen and on any other reactive sites, is attached to the resin from solution using known peptide coupling techniques. The protecting group on the alpha-amino group is removed (leaving other protecting groups, if any, intact), and the next amino acid of the desired sequence (carrying suitable protecting groups) is attached, and so on. When the desired polypeptide has been completely built up, it is cleaved from the resin support, all protecting groups are removed, and the polypeptide is recovered. Examples of suitable protecting groups are: alpha-tert-concentrated butyloxycarbonyl for the alpha-amino-group; benzyl, 4-methoxybenzyl, or 4-methylbenzyl for the thiol group of cysteine, the beta-carboxylic acid group of aspartic acid, the gamma-carboxylic acid group of glutamic acid and the hydroxyl groups of serine, threonine, and tryosine; benzyloxycarbonyl or a 2-chloro- or 3, 4-dimethoxy-derivative thereof for the ring nitrogens of histidine and tryptophan and the epsilon-amino group of lysine; p-nitrophenyl for the amide nitrogens of asparagine and glutamine; and nitro or tosyl for the guanidine group of arginine.

For the purposes of this disclosure, accepted shorthand designations of the amino acids have been used. A complete listing is provided herein below:

| One and Three-letter Amino Acid Abbreviations | | |
| --- | --- | --- |
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |
| B | Asx | Asp or Asn, not distinguished |
| Z | Glx | Glu or Gln, not distinguished |
| X | X | Undetermined or atypical amino acid |

Among the claimed peptides 15 amino acid residues in length there are overlaps of five and ten amino acids. For example, the claimed peptides LCDLAPEAPPPTLPP and PEAPPPTLPPDMAQV have an overlap of a ten amino acid sequence, PEAPPPTLPP. In an additional example the claimed peptides VKYAGSQVASTSEVL and PSELRRIASQVKYAG have an overlap of a five amino acid sequence, VKYAG. The significance of this overlap is that a five amino acid sequence can provide the inhibitory action found in the claimed peptides 15 amino acid residues in length. Therefore, it is foreseeable from the inhibitory activity of a five amino acid sequence that a two amino acid sequence found within any of the claimed peptides would also have inhibitory activity for vWF binding.

It has been found through experimentation that the addition of at least one R and/or K residue to peptides which inhibit platelet-fibrinogen binding and platelet aggregation enhances the inhibitory activity of these peptides. In view of this ability to enhance inhibition of such binding and aggregation, peptides with R and/or K residues extending from the amino-or carboxy-termini of peptides have utility wherever it is desirable to retard or prevent the formation of a thrombus or clot in the blood (i.e. anti-thrombotic activity).

Because these different claimed peptides are from different parts of the 52/48 kDa fragment it is possible there is more than one binding site for GPIb and heparin. Therefore, mixing and/or linking two or more of these claimed peptides may make a more potent inhibitor.

One or more of the peptides of the present invention can be formulated into pharmaceutical preparations for therapeutic, diagnostic, or other uses. To prepare them for intravenous administration, the compositions are dissolved in water containing physiologically compatible substances such as sodium chloride (e.g. 0.35-2.0 M), glycine, and the like and having a buffered pH compatible with physiological conditions. The amount to administer for the prevention of thrombosis will depend on the severity with which the patient is subject to thrombosis, but can be determined readily for any particular patient.

As mentioned above, several laboratories have attempted to define specific substructural domains of vWF that are responsible for its various binding functions. Of particular importance to the present work is the report of Fujimura, et al., *J. Biol. Chem.* 261:381-385 (1986) suora. A tryptic fragment of vWF (T52/58) that completely inhibits asialo vWF-initiated platelet aggregation as well as ristocetin-induced aggregation in the presence of intact vWF is described. Moreover, this fragment inhibited ristocetin induced binding of intact $^{125}$I-vWF to platelets, but did not interfere with thrombin or ADP-induced binding. These studies provided direct evidence that the domain necessary for binding of vWF to the platelet GPIb receptor is contained within this fragment. Since this fragment retains its ability to inhibit platelet aggregation even after reduction, alkylation, extensive treatment with denaturants, or 70% deglycosylation with endo F, it is likely that a linear amino acid sequence defines this domain.

In addition to the preparation of synthetic peptides described above, this invention also contemplates the recombinant expression of fragments of von Willebrand factor. These peptides exhibit in vitro biological activity as evidenced by their ability to inhibit ristocetin induced platelet aggregation. Consequently, these recombinant peptides are also useful as in vitro antithrombotic agents that block the interaction of vWF to the GPIb receptor.

Genes coding for polypeptides such as Factor VIIIR or fragments of Factor VIIIR may be cloned by incorporating a DNA fragment coding for the polypeptide into a recombinant DNA vehicle (e.g., vector) and transforming suitable prokaryotic or eukaryotic hosts. Suitable prokaryotic hosts include but are not limited to Escherichia, Bacillus, Streptomyces and the like. Suitable eukaryotic hosts include but are not limited to yeast, such as Saccharomyces and cell cultures such as VERO, HeLa, mouse C127, Chinese hamster ovary (CHO), W138, BHK, COS-7 and MDCK. Such recombinant DNA techniques have now become well known and are described in Methods in Enzymology. (Academic Press), Volumes 65 and 68 (1979), 100 and 101 (1983), and the references cited therein. An extensive technical discussion embodying most commonly used recombinant DNA methodologies can be found in Maniatis, et al., *Molecular Cloning*, Cold Spring Harbor Laboratory (1982) or *Current Protocols in Molecular Biology*, Greene Publishing (1988).

One way of obtaining a DNA fragment encoding a desired polypeptide such as vWF is via cDNA cloning. In this process, messenger RNA (mRNA) is isolated from cells known or suspected of producing the desired protein. Through a series of enzymatic reactions, the mRNA population of the cells is copies into a complementary DNA (cDNA). The resulting cDNA is then inserted into cloning vehicles and subsequently used to transform a suitable prokaryotic or eukaryotic host. The resultant gene "library" is comprised of a population of transformed host cells, each of which contain a single gene or gene fragment. The entire library, therefore, provides a representative sample of the coding information present in the mRNA mixture used as a starting material.

Gene libraries can be screened using nucleic acid or antibody probes in order to identify specific DNA sequences. Once isolated, these DNA sequences can be modified or can be assembled into complete genes. Alternatively, as described in this invention, specific fragments of a gene can be engineered independently of the rest of the gene. Protein fragments encoded by these engineered gene fragments may not be found in nature, yet they may have significant utility in treating undesirable physiological conditions. The genetic engineering of vWF fragments for the prevention and/or the treatment of thrombosis is one such case.

The following examples are given as illustrative of the present invention. The present invention is not restricted only to these examples.

EXAMPLE 1

Inhibition of vWF binding to platelets

Divalent cation free platelets were prepared using SEPHAROSE CL-2B chromatography, and used at a concentration of $10^8$/ml in an incubation volume of 125 μl. $^{125}$I-vWF was added at a concentration of 5 μg/ml and the competing ligand, LCDLAPEAPPPTLPP at a concentration of 2.16 μg/ml. Ristocetin was then added at a concentration of 0.75 mg/ml. After 30 minutes incubation at room temperature without agitation, two 50 μl aliquots of the mixture were layered over two separate 300 μl cushions of 20% sucrose in a 500 μl Sarstedt microfuge tube (W. Germany), and bound ligand was separated from free ligand by 4 minutes centrifugation at 12,000×g in Beckman Microfuge B. The tube tips containing bound ligand were amputated and counted in a gamma counter. Nonspecific binding was determined in the presence of a 50-fold excess of unlabeled vWF added together with the labeled ligand and specific binding was calculated by substracting nonspecific binding from the total. The synthetic peptide LCDLAPEAPPPTLPP completely inhibited von Willebrand factor binding to platelets.

Table 1 lists specific peptides within the scope of the present invention and their inhibitory activities of vWF binding to platelets. The inhibitory activities of the peptides were determined according to the procedure set forth in Example 1. 100% is that amount of radiolabeled vWF which binds to platelets in the absence of any inhibitory peptides. Value less than 100% in Table 1 reflect the inhibitory activity of these peptides.

TABLE 1

| Peptide | % of vWF binding to platelets |
|---|---|
| 52/48 kDa Fragment | 0 |
| PEAPPPTLPPDMAQV | 3 |
| VKYAGSQVASTSEVL | 46 |
| RIASQVKYAGSQVAS | 44 |
| PSELRRIASQVKYAG | 17 |
| DMMERLRISQKWVRV | 26 |
| QIFSKIDRPEASRIA | 31 |
| LYVEDISEPPLHDFY | 1 |
| VSPTTLYVEDISEPP | 18 |
| VTLNPSDPEHCQICH | 19 |
| CQICHCDVVNLTCEA | 16.5 |
| SDPEHCQICHCDVVN | 45 |
| CDVVNLTCEACQEPG | 16 |
| LTCEACQEPGGLVVP | 98 |
| CQEPGGLVVPPTDAP | 16 |
| GLVVPPTDAPVSPTT | 129 |
| PTDAPVSPTTLYVED | 4 |
| ISEPPLHDFYCSRLL | 86 |
| CSRLLDLVFLLDGSS | 90 |
| DLVFLLDGSSRLSEA | 65 |
| LDGSSRLSEAEFEVL | 74 |
| RLSEAEFEVLKAFVV | 214 |
| EFEVLKAFVVDMMER | 13 |
| KAFVVDMMERLRISQ | 28 |
| LRISQKWVRVAVVEY | 110 |
| KWVRVAVVEYHDGSH | 133 |
| AVVEYHDGSHAYIGL | 100 |
| HDGSHAYIGLKDRKR | 11 |

TABLE 1-continued

| Peptide | % of vWF binding to platelets |
|---|---|
| AYIGLKDRKRPSELR | 38 |
| KDRKRPSELRRIASQ | 12 |
| SQVASTSEVLKYTLF | 60 |
| TSEVLKYTLFQIFSK | 328 |
| KYTLFQIFSKIDRPE | 142 |
| IDRPEASRIALLLMA | 110 |
| ASRIALLLMASQEPQ | 12 |
| SQEPQRMSRNFVRYV | 152 |
| RMSRNFVRYVQGLKK | 24 |
| FVRYVQGLKKKKVIV | 331 |
| IPVGIGPHANLKQIR | 9 |
| GPHANLKQIRLIEKQ | 9 |
| LKQIRLIEKQAPENK | 163 |
| LIEKQAPENKAFVLS | 54 |
| APENKAFVLSSVDEL | 60 |
| AFVLSSVDELEQQRD | 54 |
| SVDELEQQRDEIVSY | 43 |
| EQQRDEIVSYLCDLA | 79 |
| EIVSYLCDLAPEAPP | 20 |
| PTLPPDMAQVTVGPG | 31 |
| DMAQVTVGPGLLGVS | 64 |
| TVGPGLLGVSTLGPK | 7 |

EXAMPLE 2

Inhibition of vWF binding to heparin

Assays were performed in an incubation volume of 125 µl in plastic Eppendorf tubes. Heparin-SEPHAROSE CL-6B (Pharmacia), $^{125}$I-vWF and bovine serum albumin (BSA) (Sigma) were added to tubes at final concentrations of 5% (v/v), 1 µg/ml and 0.1% (w/v), respectively. Then, competing ligand, KDRKRPSELRRIASQ, in 0.05 M Tris-0.15 M NaCl-HCl buffer, pH 7.3 (TBS) was added to the incubation mixture at a concentration of 2.16 µg/ml. After 30 minutes incubation at room temperature with occasional agitation, two 50 µl aliquots of the mixture were layered over two separate 300 µl cushions of 20% sucrose in a 500 µl Sarstedt microfuge tube (W. Germany), and bound ligand was separated from free ligand by 4 minutes centrifugation at 12,000×g in Beckman Microfuge B. The tube tips containing bound ligand were amputated and counted in a gamma counter.

Nonspecific binding was determined in the presence of 10 mg/ml heparin Na salt (porcine intestinal mucosa, grade II, 162 USP units/mg) (Sigma, St. Louis, MO) added together with the labeled ligand and heparin-SEPHAROSE CL-6B gel and specific binding was calculated by subtracting nonspecific binding from the total. The synthetic peptide KDRKRPSELRRIASQ inhibited von Willebrand Factor binding to heparin by 75%.

Table 2 lists specific peptides within the scope of the present invention and their inhibitory activities of vWF binding to heparin. The inhibitory activities of the peptides were determined according to the procedure set forth in Example 2. 100% is that amount of radiolabeled vWF which binds to heparin in the absence of any inhibitory peptides. Values less than 100% in Table 2 reflect the inhibitory activity of these peptides.

TABLE 2

| Peptide | % of vWF binding to heparin |
|---|---|
| 52/48 kDa Fragment | 0 |
| LIEDQAPENKAFVLS | 53.5 |
| SQEPQRMSRNFVRYV | 56 |
| KYTLFQIFSKIDRPE | 54.5 |

TABLE 2-continued

| Peptide | % of vWF binding to heparin |
|---|---|
| DMMERLRISQKWVRV | 54.5 |
| VTLNPSDPEHCQICH | 83 |
| SDPEHCQICHCDVVN | 93 |
| CQICHCDVVNLTCEA | 92 |
| CDVVNLTCEACQEPG | 96 |
| LTCEACQEPGGLVVP | 116 |
| CQEPGGLVVPPTDAP | 91 |
| GLVVPPTDAPVSPTT | 160 |
| PTDAPVSPTTLYVED | 106 |
| VSPTTLYVEDISEPP | 91 |
| LYVEDISEPPLHDFY | 46 |
| ISEPPLHDFYCSRLL | 52 |
| CSRLLDLVFLLDGSS | 122 |
| DLVFLLDGSSRLSEA | 116 |
| LDGSSRLSEAEFEVL | 95 |
| RLSEAEFEVLKAFVV | 125 |
| EFEVLKAFVVDMMER | 88 |
| KAFVVDMMERLRISQ | 116 |
| LRISQKWVRVAVVEY | 54 |
| KWVRVAVVEYHDGSH | 162 |
| AVVEYHDGSHAYIGL | 99 |
| HDGSHAYIGLKDRKR | 67 |
| AYIGLKDRKRPSELR | 84 |
| PSELRRIASQVKYAG | 84 |
| RIASQVKYAGSQVAS | 119 |
| VKYAGSQVASTSEVL | 103 |
| SQVASTSEVLKYTLF | 93 |
| TSEVLKYTLFQIFSK | 157 |
| QIFSKIDRPEASRIA | 94 |
| IDRPEASRIALLLMA | 81 |
| ASRIALLLMASQEPQ | 73 |
| SQEPQRMSRNFVRYV | 36 |
| FVRYVQGLKKKKVIV | 188 |
| IPVGIGPHANLKQIR | 24 |
| GPHANLKQIRLIEKQ | 24 |
| LKQIRLIEKQAPENK | 5 |
| APENKAFVLSSVDEL | 190 |
| AFVLSSVDELEQQRD | 113 |
| SVDELEQQRDEIVSY | 99 |
| EQQRDEIVSYLCDLA | 93 |
| EIVSYLCDLAPEAPP | 103 |
| PTLPPDMAQVTVGPG | 94 |
| DMAQVTVGPGLLGVS | 106 |
| TVGPGLLGVSTLGPK | 30 |

EXAMPLE 3

Inhibition of vWF binding to collagen

Binding of vWF to collagen. vWF for these studies was radiolabeled with $^{125}$I following the technique described by Fraker and Speck, *Biochem. Biophys. Res. Commun.* 80:849–857 (1978), using Iodogen (Pierce Chemical, Rockford, Il). The specific activity of the preparations used in these studies varied between 2.46–8.55×10$^{-4}$ Ci/mg (or 9.13–31.7×10$^6$ Bq/mg). The collagen preparation used was obtained commercially (Hormon-Chemie, Munich, FRG) and consisted of an acid-insoluble, microfibrillar equine collagen, type I. The absence of non-collagenous contaminates was determined by analysis with SDS-PAGE (5% or 7.5% acrylamide with 5% cross linking) and reduction with 5% 2-mercaptoethanol. The gels were stained with Coomassie brilliant blue R. The definition of type I collagen was based on analysis by refractory calorimetry and amino acid composition (kindly performed by Dr. John McPherson, Collagen Corporation, Palo Alto, CA).

Each binding mixture contained 12.5 µl of the collagen suspension (1 mg/ml in isotonic glucose solution, pH 2.7), 5 µl of 0.4 M phosphate buffer (mono- and disodium), pH7, and 132.5 µl containing suitably diluted [$^{125}$I]vWF as well as other test reagents, when necessary, all in 0.02 M Tris, 0.150 M NaCl buffer, pH 7.4. The mixture also contained 0.48% bovine serum albumin (Fraction V, Calbiochem, La Jolla, CA).

Incubation was usually at room temperature (22°-25° C.) for 20 minutes, except when indicated otherwise. A 50 μl aliquot of each experimental mixture was then layered, in duplicate, over 300 μl of 20% sucrose in the above mentioned Tris buffer, containing albumin. Separation of bound from free ligand was achieved by centrifugation for 8 minutes at 12,000 g, a condition that resulted in pelleting of the insoluble collagen microfibrils while the soluble vWF remained on top of the sucrose layer. The tip of the microcentrifuge tube containing the collagen pellet was then amputated and the associated radioactivity was quantitated in a multichannel gamma-scintillation scintillation spectrometer (Packard Instruments, Downer's Grove, IL). Non-saturable (non-specific) binding was determined experimentally by adding an excess amount of unlabeled vWF into the experimental mixture. Moreover, when binding isotherms were evaluated by Scatchard-type analysis, non-saturable binding was generated as a fitted parameter from the total binding isotherm using the microcomputer-assisted program Ligand.

Inhibition with 52/48 kDa fragment. The effect of tryptic fragment 52/48 kDa on the binding of intact [$^{125}$I] vWF to collagen was evaluated. The experimental mixtures were prepared as described in the preceding paragraph, with the only difference that the 52/48 kDa fragment samples tested for their inhibitory activity were added, at concentrations of 1.24, 2.55 and 5 μM, immediately before addition of [$^{125}$I] vWF at a concentration of 2 μg/ml. The 52/48 kDa fragment inhibition of von Willebrand Factor binding to collagen was greater than 90% at the above noted concentrations. It should be noted that the type of collagen employed may influence the assay. It is, therefore, preferred to use equine collagen, Type I as described herein.

EXAMPLE 4

Expression of the 52 kDa vWF fragment

FIG. 1 indicates a diagrammatic representation of full-length vWF cDNA based on the nucleotide sequence described in Sadler et al. Proc. Nat'l. Acad. Sci. USA 82:6349 (1985) supra, and Shelton-Inloes et al. Biochemistry, 25:3164 (1986) supra. The 52 kDa tryptic fragment of vWF that binds to the platelet GPIb receptor is encoded by the central portion of the cDNA from amino acid residue 449 to residue 728 described by Titani et al. Biochemistry, 25:3171 (1986) supra. A cDNA clone encoding this region was provided by Dr. Dennis Lynch of Dana Farber Cancer Institute. The clone was originally isolated from a human umbilical vein endothelial cell cDNA library, and contained a 4 kb insert cloned via EcoRI linkers into the EcoRI site of pBR322. An EcoRI/SacI fragment from this clone was subcloned into GEMII to yield the vector pMMB1 (See FIG. 2). Nucleotide sequence analysis of pMMB1 indicated that an 857 bp MstII-NcoI fragment encodes the region of interest and contains only a few extra amino acid residues at both the amino and carboxy terminus when compared to the 52/48 fragment (See FIG. 1). The phrase "consists essentially of" as used herein to describe a specific amino acid sequence admits the possibility of the addition or deletion of a small number of biologically insignificant amino acids residues to the specific sequence. For example the peptide fragment encoded by recombinant plasmids disclosed herein have 5 amino acid residues preceeding the defined position 449 and six amino acid residues following the defined position 728. These additions resulted from the particular cloning strategy employed and to not affect the biological activity of the defined peptide and as such do not materially affect the basic and novel characteristics of the composition.

Three vectors were used to demonstrate vWF fragment expression in E. coli. Vector pMMB3 used the highly efficient $P_R$ promoter from bacteriophage lambda. Induction of vWF fragment expression in E. coli can be achieved by growing the cells to mid-log phase at 30° C. and then shifting the temperature to 42° C. The second vector (pMMB5) used the hybrid trp-lac (tac) promoter system that is regulated by the lac repressor. Induction in this system is achieved by growing cells to mid-log phase at 37° C. followed by the addition of the lactose analog IPTG. The results obtained with pMMB3 and pMMB5 were very similar. Briefly, E. coli cells transformed with each of the above plasmids were grown to mid-log phase, induced for 1-16 hours, harvested, and fractionated into soluble and insoluble components. In both constructs the vWF fragment was produced at approximately 0.5% of total cell protein, and showed a similar time course of induction. Additionally, the vWF fragment exhibited extreme insolubility following lysis of either population of cells.

The third vector used for expression of the vWF fragment contained a promoter from the bacteriophage T7. In this system, the vWF DNA is placed into a vector containing the promoter and translation initiation signals for the Tφ protein of bacteriophage T7. T7 RNA polymerase can then be delivered to the host cell by either induction or infection. In the present example the vWF expression vector was placed into a cell that carries a prophage containing the gene for T7 RNA polymerase under control of the lac UV5 promoter. Addition of the lactose analog IPTG to a growing culture of cells induces T7 RNA polymerase, which in turn transcribes the target DNA in the plasmid. Transcription by T7 RNA polymerase is so active that target RNA can accumulate to amounts comparable to ribosomal RNA and target proteins can constitute the majority of cellular protein.

As an initial characterization of the synthesis of vWF fragment, cells were induced and samples taken at time points between 0.5 and 16 hours post induction. These data indicated that by 4 hours post induction, vWF fragment constituted approximately 25% of total cellular protein (FIG. 9). This level was much higher than either the tac or $P_R$ vectors described above. For this reason, all subsequent work was performed with the T7 vector constructs.

Regardless of the vector system employed, the recombinant proteins were biologically active in that they inhibited botrocetin induced binding of intact $^{125}$I-vWF to platelets and also inhibited ristocetin-induced platelet aggregation in the presence of intact vWF.

A. Construction of the $P_R$ Expression Vector

The plasmid pDS19 was obtained from Dr. Dorothea Scandella, American Red Cross, Rockville, MD. This plasmid is a derivative of pCQV2 (Queen, J. Mol. and Appl. Genet., 2:1 (1983)), and was used to provide a strong promoter, $P_R$ from bacteriophage lambda, a ribosome binding site, and an ATG translation initiation codon. The ATG codon overlapped a BamHI restriction site (GGATCC) as follows: ATGGATCC. pDS19 also contains the phage lambda cI857 temperature sensitive repressor which blocks transcription from $P_R$ at 30° C. but not at 42° C. Expression of a gene placed 3' to $P_R$ in this vector can thus be induced by shifting the temperature from 30° C. to 42° C.

The strategy for cloning the DNA fragment encoding the 52,000 Da protein into pDS19 is shown in FIG. 2. All enzymes were used as suggested by the manufacturer.

pDS19 (10 μg) was digested with 20 U of BamHI and 10 U of SphI (Boehringer Mannheim) for 2 hours at 37° C. The DNA was then gel purified using Low Melting Point agarose (Bethesda Research Laboratories). The large fragment was excised and melted at 70° C., phenol extracted, and ethanol precipitated. Oligonucleotide linkers were added as shown in FIG. 2. The complementary oligonucleotides were annealed in 100 mM NaCl-10 mM Tris pH 7.8, 1 mM ETDA by heating at 65° C. for 10 minutes followed by slow cooling to room temperature. Twenty pmoles of the annealed oligonucleotides were ligated to 500 ng of pDS19 (BamHI, SphI) with 2.5 U T4 DNA ligase (Boehringer Mannheim) for 18 hours at 15° C. 5 ng of the ligation mixture was used to transform E. coli HB101 (BRL) and plated on LB agar and 100 μg/ml ampicillin at 30° C. The presence of the oligonucleotide linker was determined by restriction endonuclease analysis of plasmid DNA isolated from transformed colonies. Plasmid DNA from a single positive isolate was referred to as pMMB2 and was used for further constructions described below.

pMMB2 (10 μg) and a vWF cDNA clone designated pMMBI (20 μg) were digested with MstII and NcoI (New England Biolabs) for 2 hours at 37° C. The large vector fragment and the 857 bp vWF fragment were gel purified as described below. The fragment (100 ng) was ligated to 400 ng of pMMB2 vector in the presence of 2.5 U T4 DNA ligase (Boehringer Mannheim) at 15° C. for 18 hours. As above, 5 ng of the ligation mixture was used for transformation. Plasmid DNA was isolated from individual transformants and the presence of the vWF insert was determined by restriction endonuclease cleavage analysis. A single positive isolate designated pMMB3 was used for expression of vWF fragment as described below (Section E). The complete nucleotide sequence of the coding portion of pMMB3 is indicated in FIG. 3.

B. Construction of the tac Expression Vector

FIG. 4 is a diagrammatic representation of the construction of the tac vector for expression of the 52 kDa vWF fragment. The plasmid pDS17 was obtained from Dr. Dorothea Scandella, American Red Cross, Rockville, MD. This plasmid is a derivative of ptac12 (Amann et al. Gene 25:167 (1983)) and was used to provide a strong promoter, $P_{tac}$, a ribosome binding site, and a transcription terminator. Synthetic oligonucleotides were used to supply the ATG translation start signal as well as restriction enzyme sites to facilitate cloning of vWF cDNA.

pDS17 (10 μg) was digested with 20 U of PvuII and 20 U of HindIII (Boehringer Mannheim) for 2 hours at 37° C. The DNA was then gel purified using Low Melting Point agarose (Bethesda Research Laboratories). The large fragment was excised and melted at 70° C., phenol extracted, and ethanol precipitated. Oligonucleotide linkers were added as shown in FIG. 4. The complementary oligonucleotides were annealed in 100 mM NaCl-10 mM Tris pH 7.8, 1 mM EDTA by heating at 65° C. for 10 minutes followed by slow cooling to room temperature. Twenty pmoles of the annealed oligonucleotides were ligated to 500 ng of pDS17 (PvuII, HindIII) with 2.5 U T4 DNA ligase (Boehringer Mannheim) for 18 hours at 15° C. 5 ng of the ligation mixture was used to transform E. coli JM101 (BRL) and plated on LB agar and 100 μg/ml ampicillin at 37° C. The presence of the oligonucleotide linker was determined by restriction endonuclease analysis of plasmid DNA isolated from transformed colonies. Plasmid DNA from a single positive isolate was referred to as pMMB4 and was used for further constructions described below.

pMMB4 (10 μg) and the $P_R$ expression vector designated pMMB3 (20 μg) were digested with MstII and SohI (New England Biolabs) for 2 hours at 37° C. The large vector fragment and the 880 bp vWF fragment were gel purified as described above. The fragment (100 ng) was ligated to 400 ng of pMMB4 vector in the presence of 2.5 U T4 DNA ligase (Boehringer Mannheim) at 15° C. for 18 hours. As above, 5 ng of the ligation mixture was used for transformation of E. coli K12 JM101. Plasmid DNA was isolated from individual transformants and the presence of the vWF insert was determined by restriction endonuclease cleavage analysis. A single positive isolate designated pMMB5 was used for expression of vWF fragment as described below (Section F).

C. Construction of the T7 Expression Vector

FIG. 5 indicates a diagrammatic representation of the construction of the T7 vector for expression of the 52 kD vWF fragment. The plasmid pET-8c was obtained from Dr. F. William Studier of Brookhaven National Laboratories. This plasmid contains a fragment of T7 DNA specifying the gene 10 promoter inserted into the BamHI site of pBR322 so as to direct transcription counterclockwise. This plasmid also provides a transcription terminator for T7 RNA polymerase, a ribosome binding site and an ATG for translation initiation with the ATG overlapping an NcoI restriction site (CCATGG).

The vector DNA (pET-8c) was digested with NcoI and the linear plasmid DNA was gel purified on Low Melting Point agarose as described above. Similarly, the insert containing plasmid (pMMB5) was digested with SphI and the 3' protruding termini made blunt ended by incubation with T4 DNA polymerase. Following cleavage with MstII the vWF fragment was gel purified as above.

The insert fragment (100 ng) and the vector (450 ng) were mixed and incubated in the presence of deoxyribonucleotides and the Klenow fragment of DNA polymerase I to fill-in protruding 5' termini. The vector DNA and the insert DNA were then ligated using T4 DNA ligase and the product used to transform E. coli DH-1. A clone containing the insert DNA in the correct orientation was identified and further confirmed by DNA sequence analysis.

To direct expression of the vWF gene, the recombinant plasmid was transferred into E. coli BL21 (DE3)pLysS, a lambda lysogen of BL21 (rB−mB−rif$_s$) in which the prophage carries a copy of the gene for T7 RNA polymerase under control of the lac UV5 promoter (Studier and Moffett, J. Mol. Biol. 189, 113–130 (1986)). This strain also contains a plasmid (pLysS) that directs expression of T7 lysozyme which serves to increase the tolerance of the host for maintaining toxic target plasmids (Studier et al., "Methods Enzymol.", In Press).

Host BL21 (DE3) cells without the pLysS plasmid have also been used and express the 52/48 fragment at an equivalent level. These strains grow more slowly but appear to be more stable in storage when compared to the pLysS containing host. Downstream processing considerations not related to the invention as claimed herein may dictate the use of one or the other of these strains or a different host entirely.

D. Construction of the Kanamycin Resistant T7 Expression Vector

A plasmid (pET-8c(Km$^R$)) containing the T7 promoter and conferring resistance to kanamycin was obtained from Dr. F. William Studier of Brookhaven National Laboratories. The plasmid was constructed by removing the ampicillin resistance gene from pET-8c via excision of a BspHI-EcoRI fragment (pBR322 bp 3195-4361) and replacing it with an 869 bp fragment encoding kanamycin resistance (Km$^R$), with the Km$^R$ gene oriented clockwise in the vector. The Km$^R$ gene derives from Tn903 (Oka et al., *J. Mol. Biol.* 147:217-226 (1981)) and was obtained using the polymerase chain reaction with pUC4KISS (Barany F., Gene 37:111-123 (1985)) as template. The fragment carrying the Km$^R$ gene starts 50 nucleotides ahead of the Km$^R$ initiation codon and ends exactly at the termination codon.

A plasmid expressing the vWF fragment and conferring resistance to kanamycin was constructed from pET-8c52K (FIG. 5) and pET-8c(Km$^R$). Briefly, an XbaI/BamI fragment encoding the vWF fragment was excised from pET-8c 52K and ligated into XbaI/BamHI cleaved pET-8c(Km$^R$). The resulting plasmid DNA (pET-8c52K(Km$^R$)) was transformed into *E. coli* DH-1 cells and a single isolate was identified that released the appropriate size fragment by digestion with XbaI/BamHI. DNA from this isolate was then used to transform *E. coli* BL21 (DE3) pLysS. A single isolate from this transformation was then used for expression of vWF fragment as described below (Section F).

E. Expression of vWF Fragments in the P$_R$ Expression Vector

Plasmid DNA of pMMB3 was used to transform competent *E. coli* K12 HB101. Cultures of the transformed cells were grown in LB medium+50 µg/ml ampicillin at 30° C. until they reached A$_{595}$ of 0.4. They were shifted to 42° C. for 5 minutes and incubated further for a total of two hours at 40° C. The cells were pelleted by centrifugation and suspended in 0.1 volume sample buffer (Laemmli, *Nature*, 227:680 (1970)), and boiled 10 minutes.

F. Expression of vWF Fragments in the tac and T7 Expression Vectors

Overnight cultures of transformed cells were grown in LB media containing selective antibiotics. Cultures of T7 vector were selected in 100 µg/ml ampicillin or 30 µg/ml kanamycin in addition to 30 µg/ml chloramphenicol to select for pLysS. Cultures of the tac expression vectors were selected on ampicillin alone. Overnight cultures of transformed cells were diluted 1:100 and grown in LB medium at 37° C. until they reached A$_{595}$ of 0.4. Cultures were induced by adjusting to 0.5 mM IPTG and then incubated further for various times at 37° C. The cells were pelleted by centrifugation and suspended in 0.1 volume sample buffer (Laemmli, Nature 227:680 (1970)) and boiled 10 minutes.

G. Western Blot Analysis of vWF Fragments

Aliquots of approximately 50 µg protein from steps E and F above, were subjected to electrophoresis on 12% polyacrylamide-SDS gels (Laemmli, supra) and electroblotted onto nitrocellulose paper (Schleicher & Schuell, BA85). Procedures for electroblotting and reaction with antibodies were performed following procedures supplied by BioRad, Inc.

The primary antibodies used were either a rabbit polyclonal antibody specific for vWF or the RG46 monoclonal antibody, (Fujimura, et al., supra) specific for the 52Kd tryptic fragment of vWF. The primary antibody was incubated with nitrocellulose paper for 15 hours at 23° C. The secondary antibody was either affinity purified biotinylated goat antirabbit or goat anti-mouse and was incubated for 30 minutes at 23° C. at a 1:10,000 dilution. After washing, the blot was treated with a streptavidin-biotin-horseradish-peroxidase conjugate as per manufacturers instructions (Vector Laboratories). A color development reagent obtained from BioRad (4-chloro-1-napthol) was used to visualize the vWF protein bands.

H. Platelet Aggregation

Platelet aggregation studies were carried out at a final platelet concentration of $1.6 \times 10^8$/ml in a Bio-data PAP-4 aggregometer with 0.2 ml of fixed washed platelets.

I. Characterization of cMMB3 and pMMB5 Expression

As mentioned above the results obtained with pMMB3 and pMMB5 were very similar. Briefly, *E. coli* cells transformed with each of the above plasmids were grown to mid-log phase, induced for 1-16 hour, harvested, and fractionated into soluble and insoluble components. In both constructs the vWF fragment was produced at approximately 0.5% of total cell protein, and showed a similar time course of induction.

The vWF fragment exhibited extreme insolubility following lysis of either population of cells (FIG. 6, lanes 1-3). Additionally, washing the insoluble inclusion bodies with 2M urea resulted in approximately 5% of the total protein being released into the supernatant as well as substantial quantities of DNA.

Although, this supernatant contained some vWF fragment (FIG. 6, lane 4) the majority remained insoluble in 2M urea (FIG. 6, lane 5).

In order to obtain soluble material, the washed inclusion bodies were dissolved in 6M Guanidine hydrochloride, 10 mM DDT and then alkylated using iodoacetamide. The reduced and alkylated fragment was then subjected to gel filtration on Sephacryl S-200 equilibrated in 6M urea 0.1 M acetic acid. A typical elution profile is shown in FIG. 7. Fractions containing immunoreactive vWF fragment were pooled, dialyzed and concentrated via ultrafiltration. SDS gel electrophoresis followed by staining with Coomasie blue indicated that the material was 50-75% pure at this stage of purification.

The material purified by gel filtration was next examined for its ability to inhibit in vitro platelet aggregation. The data shown in FIG. 8 indicates that two different concentrations of the recombinant vWF fragment causes a dose-dependent reduction in ristocein induced platelet aggregation. This reduction was similar to the reduction caused by the concentration of the non-recombinant vWF fragment (data not shown). Additionally, the same concentrations of a recombinant fragment of Factor VIIIC purified in an identical fashion failed to inhibit ristocetin-induced platelet aggregation (data not shown). Experiments indicate that the recombinant vWF fragment prepared from the T7 promoter constructs inhibited ristocetin-induced platelet aggregation in an identical fashion to the fragment purified from the $P_R$ promoter constructs.

J. Isolation and Characterization of vWF Produced by the Recombinant T7 Expression System In order to obtain sufficient material for biochemical characterization, cells were collected and used for protein purification. Lysis of the cells followed by a brief centrifugation yielded an insoluble fraction that was enriched for vWF fragment. Further purification of this fraction by solubilization in 6M Guanidine hydrochloride followed by reduction, alkylation and ion exchange chromatography on Q-SEPHAROSE yielded essentially homogeneous fragment (FIG. 9, lane 6), that was soluble in physiological solutions and having an apparent molecular weight of about 33,000Da. (+/−1,000). Accordingly, a seed culture was grown up overnight at 37° in medium containing chloramphenicol (25 mg/liter) and kanamycin (30 mg/liter). Fermentation was carried out at a scale of 50 liters, at 37° C., in an MPP 80 fermenter (manufactured by New Brunswick Scientific). Fermentation was carried out at pH 7, maintained by microprocessor controlled addition of either $NH_4OH$ or $H_3PO_4$ as needed. Foaming was maintained at pre-determined levels by the microprocessor controlled addition of antifoam (Mazu DF 204). The overnight seed culture (0.5 liter) was transferred to the fermenter which has been prepared with 50 liters of medium (Water for injection is used for medium preparation. NZY Broth (BBL, catalogue #99309) is dissolved at 21 grams/liter in warm water for injection. The dissolved medium is filtered through a glass fiber prefilter, then through a 0.22 micron filter. The filtration removes material which otherwise discolors the inclusion bodies.) The 50 liter batch of medium in the fermenter was prepared without antibiotics—the only antibiotics present are the residual chloramphenicol and kanamycin carried over in the 0.5 liter seed. The bacteria were grown with agitation (impeller at 200 RPM), and with aeration of 0.5 volumes of air per volume of liquid per minute. A typical timecourse of the growth and induction showed that the measured oxygen levels decrease as the cells grow. Induction was usually begun after approximately three hours growth, when cells have reached an $OD_{595nm}=0.8-1.0$ after which time the oxygen had declined to about 60% saturation.

Induction of expression was by addition of IPTG (isopropyl-beta-D- thiogalactopyranoside) to reach a final concentration of 0.4 mM. Induction with IPTG caused the culture to grow more slowly. Agitation was maintained at 200 RPM. It was routinely observed that the dissolved oxygen rises during the induction period. Induction proceeded for approximately three hours, after which fermentation was stopped.

Cells were harvested and concentrated using hollow fiber microfilter membrane cartridges. Two Amicon H5MPO1-43 filter cartridges were employed in a recirculating mode. Cells were concentrated to a volume of 2 to 4 liters on the Amicon filters, after which the cells were washed by diafiltration in the Amicon filtration apparatus with 5 volumes, approximately 10 to 20 liters, of Tris buffered saline (A-1 - TRIS BUFFERED SALINE: 0.025 M TRIS, 3.03 gms/liter $H_2O$, 0.2 M NaCl, 11.7 gms/liter $H_2O$, Final pH 7.5±0.2, 25° C.)

Cells were recovered from filtration in 4 liters of Tris buffered saline (A-1). In preparation for disrupting the cells, sodium deoxycholate was added to the cell suspension to reach a final concentration of 0.5 g/liter. The cells were mechanically disrupted by passage through a Microfluidizer ® immediately after collection. After the cells had passed once through the Microfluidizer ®, a second detergent, Tween 80 was added to the suspension of lysed cells to reach a final concentration of 0.025%. (A-2 - 2.5% (v/v) TWEEN 80: 2.5% TWEEN 80 (v/v), 25 ml/liter TBS). Heat TBS Buffer A-1 and add Tween 80 dropwise into the solution and mix until it is visably homogeneous. The solution is cooled to room temperature and then added to the disrupted cell suspension to yield a final concentration of 0.025% (v/v).) If the Tween is present in the first passage, the Microfluidizer ® can become obstructed and will require clearing the flowpath before cells can be disrupted.

After the cells have been disrupted, the suspension was centrifuged (10,000×g; 35 minutes, 4° C.) to separate the inclusion bodies, which are primarily product, from the soluble cell debris. At this stage, the inclusion bodies may be stored overnight at −20° C.

The inclusion bodies were resuspended in 35 ml of Tris buffer A-3 per gram of inclusion body wet weight, determined by difference in weight of the centrifuge tube (A-3 - TRIS BUFFER A-3: 0.05 M TRIS, 6.06 gms/liter $H_2O$, 1.21 mM sodium deoxycholate, 0.5 gms/liter $H_2O$, 2 mM dithiothreitol (DTT), 0.31 gms/liter $H_2O$, 2 mM EDTA, 0.74 gms/liter $H_2O$, 5% (v/v) glycerol, 50 ml/liter $H_2O$, 0.025% (v/v) TWEEN 80, 10 ml 2.5% TWEEN 80 (A-2)/liter $H_2O$, Final pH 9.0±0.2, 25° C.) The inclusion body pellets were routinely resuspended in buffer by using a Polytron homogenizer (Brinkmann). The resuspended inclusion bodies were passed through the Microfluidizer ® to assure thorough mixing with the buffer. After passage through the Microfluidizer ®, the inclusion bodies were collected by centrifugation. The wash procedure was carried out a total of three times with Tris buffer A-3. At the end of the third wash, the pelleted inclusion bodies are resuspended in Tris buffer A-4, which does not contain the detergents deoxycholate or Tween (A-4 - TRIS BUFFER A-4: 0.05 M TRIS, 6.06 gms/liter $H_2O$, 2 mM dithiothreitol (DTT), 0.31 gms/liter $H_2O$, 2 mM EDTA, 0.74 gms/liter $H_2O$, 5% (v/v) glycerol, 50 ml/liter $H_2O$, Final pH 9.0±0.2, 25° C.

The fourth and last wash was carried out with Tris buffer A-4. The crude product was collected after centrifugation, drained dry, and may be stored at −70° C. The overall mass yield is 70%. Pellets were redissolved in sufficient 6M Guanidine hydrochloride, 50 mM Tris pH 8.8 to place the fragment in solution.

The mixture was then adjusted to 10 mM DTT, incubated at 37° C. for 1 hour under $N_2$ and then adjusted to 50 mM iodoacetamide followed by an additional 1 hour at 37° C. DTT was again added to give a final concentration of 20 mM and the sample immediately dialyzed against Buffer C (25 mM Tris pH 8.0, 0.1 mM EDTA, 0.1 mM DTT, 20 mM KCl, 6M Urea).

The reduced and alkylated fragment was then subjected to Q-SEPHAROSE ion exchange chromatography. The sample was loaded on the column in Buffer C and then eluted with a gradient of 20–500 mM KCl in Buffer C. Reactions containing vWF fragment were pooled, dialyzed and concentrated via ultrafiltration.

The binding of vWF to glycoprotein Ib was measured in two experimental systems, in the presence of either ristocetin or botrocetin as modulators of binding. The inhibitory effect of the recombinant 52/48 kDa fragment was measured as a function of its concentration. In the assay, platelets were used at a final count of 1×10⁸/ml, ¹²⁵I-labeled vWF was at the concentration of 2 μg/ml, and ristocetin or botrocetin were used at 1.0 mg/ml or 0.4 μg/ml, respectively. The method for measuring vWF binding has been reported in detail in Ruggeri et al., *J. Clin. Invest.*, 72:1–12, 1983. The assays employing ristocetin or botrocetin are identical, except for the use of one modulator or the other.

The results of these studies are shown in FIG. 10. In the top panel (FIG. 10 A) it can be seen that the recombinant 52/48 kDa fragment apparently fails to inhibit ristocetin-induced binding of vWF to glycoprotein Ib. The amount of vWF bound is actually increased paradoxically in the presence of the recombinant fragment. These results are the consequence of precipitation of the recombinant fragment in the presence of ristocetin. The molecular aggregates formed in these mixtures include radiolabeled vWF, so that radioactivity is precipitated with the platelets when these are separated from the soluble components of the assay mixture by centrifugation. The occurrence of precipitation was demonstrated in experiments where platelets were omitted from the incubation mixture, by showing that radioactivity was still precipitated by centrifugation. Thus, in this case, the presence of precipitated radioactivity is not expression of vWF binding to platelets, and the ristocetin-dependent assay is not a valid method to test the possible inhibitory effect of the recombinant 52/48 kDA fragment. Although ristocetin may be appropriate in evaluating apparent platelet aggregation (e.g. FIG. 8), a botrocetin-based assay is preferred for competition/inhibition studies.

The results presented in the bottom panel (FIG. 10B) clearly demonstrate that the recombinant vWF fragment inhibits binding of intact vWF to platelets in the presence of botrocetin. The dose-dependent inhibitory effect is compared to that of a proteolytic fragment of vWF, designated as 116 kDa, which is known to retain the native conformation of this domain of the molecule (Mohri et al., *J. Biol. Chem.*, 264:17361–17367, 1989). In this assay system, the recombinant 52/48 kDa fragment at a concentration of 2 μmol/L completely inhibits the binding of intact vWF to glycoprotein Ib.

Experiments were performed to demonstrate that the recombinant 52/48 kDa fragment of vWF binds to platelet glycoprotein Ib like the parent molecule. This demonstration proves that the inhibitory effect of the fragment on the platelet binding of the parent molecule is due to competitive occupancy of the platelet membrane receptor, and not to other unforeseen effects on the vWF molecule itself. One possible approach was to perform direct binding studies with the labeled recombinant fragment. However, labeling of the recombinant 52/48 kDa fragment with ¹²⁵I, the standard approach for this kind of assays, resulted in an unstable molecule that could not be used in direct binding assays because of excessive nonspecific interactions. Therefore, these studies were based on the concept that binding of the recombinant molecule to the vWF-binding site of glycoprotein Ib should result in inhibition of binding of relevant monoclonal antibodies directed at epitopes overlapping with the functional site, but should have no effect on the binding of antibodies directed at other epitopes of glycoprotein Ib. Thus, two anti-glycoprotein Ibα antibodies, one inhibiting botrocetin-mediated vWF binding to platelets (LJ-Ib10) and the other with no inhibitory effect (LJ-P3), were labeled with ¹²⁵I. The effect of the recombinant 52/48 kDa fragment on antibody binding to platelets was studied in the presence or absence of botrocetin, and the results are shown in FIG. 11. In the presence of botrocetin, the recombinant fragment inhibited binding of the inhibitory anti-glycoprotein Ib antibody to platelets (FIG. 11B), but not binding of the noninhibitory antibody (FIG. 11A). In the absence of botrocetin, the recombinant fragment had no effect on the binding of either antibody. Thus, in the presence of botrocetin, the recombinant fragment appears to bind to glycoprotein Ib at a site overlapping with the epitopoe of the inhibitory antibody LJ-Ib10, without interfering with the binding of the noninhibitory antibody LJ-P3. The inhibitory effect on vWF binding to glycoprotein Ib, therefore, appears to be related to the binding of the recombinant fragment to a specific functional site on glycoprotein Ibα.

Deposit of Strains Useful in Practicing the Invention

A deposit of biologically pure culture of the following strain was made with the American Type Culture Collection, 12301 Parklawn Drive, Rockville, Md., the accession number indicated was assigned after successful viability testing, and the requisite fees were paid. Access to said culture will be available during pendency of the patent application to one determined by the Commissioner to be entitled thereto under 37 C.F.R. §1.14 and 35 U.S.C. §122. All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture(s) of the same taxonomic description.

| Strain/Plasmid | ATCC No. | Deposit Date |
| --- | --- | --- |
| BL21(DE3)pLysS/pET-8c52K(Km^R) | 68306 | April 17, 1990 |

What is claimed is:

1. A peptide capable of inhibiting the binding of von Willebrand Factor to platelets, heparin and collagen consisting essentially of an amino acid sequence corresponding to a von Willebrand Factor fragment having an amino- terminal residue about amino acid 449 Val and having a carboxy-terminal residue about amino acid 728 Arg.

2. A peptide according to claim 1 that is glycosylated and has a molecular weight of about 52/48 kDa on SDS-PAGE.

3. A peptide capable of inhibiting the binding of von Willebrand Factor to platelets and selected from the group of peptides consisting of:

LCDLAPEAPPPTLPP; PEAPPPTLPPDMAQV; VKYAGSQVASTSEVL;
SDPEHCQICHCDVVN; CDVVNLTCEACQEPG; CQEPGGLVVPPTDAP;
PTDAPVSPTTLYVED; RIASQVKYAGSQVAS; PSELRRIASQVKYAG;
DMMERLRISQKWVRV; EFEVLKAFVVDMMER; KAFVVDMMERLRISQ;
HDGSHAYIGLKDRKR; QIFSKIDRPEASRIA; LYVEDISEPPLHDFY;

-continued

| | | |
|---|---|---|
| VSPTTLYVEDISEPP; | AYIGLKDRKRPSELR; | KDRKRPSELRRIASQ; |
| ASRIALLLMASQEPQ; | RMSRNFVRYVQGLKK; | VTLNPSDPEHCQICH; |
| CQICHCDVVNLTCEA; | IPVGIGPHANLKQIR; | GPHANLKQIRLIEKQ; |
| SVDELEQQRDEIVSY; | EIVSYLCDLAPEAPP; | PTLPPDMAQVTVGPG; |
| TVGPGLLGVSTLGPK; | CSRLLDLVFLLDGSS; | LDGSSRLSEAEFEVL; |
| AFVLSSVDELEQQRD; | EQQRDEIVSYLCDLA; | LIEKQAPENKAFVLS; and |
| APENKAFVLSSVDEL. | | |

4. A peptide according to claim 3 having the sequence LCDLAPEAPPPTLPP.

5. A peptide according to claim 3 having the sequence PEAPPPTLPPDMAQV.

6. A peptide according to claim 3 having the sequence LYVEDISEPPLHDFY.

7. A peptide according to claim 3 having the sequence CQEPGGLVVPPTDAP.

8. A peptide capable of inhibiting the binding of von Willebrand Factor to heparin and selected from the group of peptides consisting of:

| | | |
|---|---|---|
| KDRKRPSELRRIASQ; | LIEKQAPENKAFVLS; | SQEPQRMSRNFURYV; |
| KYTLFQIFSKIDRPE; | DMMERLRISQKWVRV; | LYVEDISEPPLHDFY; |
| ISEPPLHDFYCSRLL; | SQEPQRMSRNNFVRYV; | IPVGIGPHANLKQIR; |
| GPHANLKQIRLIEKO; | LKQIRLIEKQAPENK; | LDGSSRLSEAEFEVL; |
| EFEVLKAFVVDMMER; | LRISQKWVRVAVVEY; | HDGSHAYIGLKDRKR; |
| AYIGLKDRKRPSELR; | and TVGPGLLGVSTLGPK | and combinations thereof. |

9. A peptide according to claim 8 having the sequence KDRKRPSELRRIASQ.

10. A peptide according to claim 8 having the sequence LKQIRLIEKQAPENK.

11. A peptide according to any one of claims 2–7 wherein at least one additional amino acid R extends from the amino or carboxy-terminus of said peptide.

12. A peptide according to any one of claims 8–10 wherein at least one additional amino acid R extends from the amino or carboxy-terminus of said peptide.

13. A peptide according to any one of claims 2–7 wherein at least one additional amino acid K extends from the amino or carboxy-terminus of said peptide.

14. A peptide according to any one of claims 8–10 wherein at least one additional amino acid K extends from the amino or carboxy-terminus of said peptide.

15. A peptide according to any one of claims 2–7 wherein at least two or more amino acids R and K extends from the amino or carboxy-terminus of said peptide.

16. A peptide according to any one of claims 8–10 wherein at least two or more amino acids R and K extends from the amino or carboxy-terminus of said peptide.

17. A therapeutic composition for use in a patient comprising an amount of the peptide according to claim 1 effective to inhibit binding of von Willeband Factor to platelets, heparin and collagen and a pharmaceutically acceptable carrier.

18. A peptide according to claim 8 having the sequence DMMERLRISQKWVRV.

19. A method of inhibiting thrombosis in a patient which comprises administering to such patient an effective antithrombotic amount of a peptide according to claim 1.

20. A peptide capable of inhibiting the binding of von Willebrand Factor to heparin having an amino acid sequence consisting essentially of PSELRRIASQ-VKYAG.

21. A peptide according to claim 3 having the sequence LIEKQAPENKAFVLS.

22. A peptide according to claim 3 having the sequence APENKAFVLSSVDEL.

23. A peptide according to claim 3 having the sequence CSRLLDLVFLLDGSS.

24. A peptide according to claim 3 having the sequence LDGSSRLSEAEFEVL.

25. A peptide capable of inhibiting the binding of von Willebrand Factor to platelets, heparin and collagen consisting essentially of an amino acid sequence corresponding to a von Willebrand Factor fragment having an amino-terminal residue about amino acid 444 Ala and having a carboxy-terminal residue about amino acid 733 Val.

26. A peptide according to claim 1, 2 or 25 in which the cysteine residues thereof are reduced and alkylated.

27. A therapeutic composition for use in a patient comprising an amount of one or more peptides according to any one of claims 2–7, 11, 13, 15, 18 or 20 effective to inhibit binding of von Willebrand Factor to platelets and a pharmaceutically acceptable carrier.

28. A method of inhibiting thrombosis in a patient which comprises administering to such patient an effective amount of a peptide according to any one of claims 2–7, 11, 13, 15, 18 or 20.

* * * * *